(12) United States Patent
Mou et al.

(10) Patent No.: US 11,744,474 B2
(45) Date of Patent: *Sep. 5, 2023

(54) BLOOD PRESSURE MEASUREMENT MODULE

(71) Applicant: Microjet Technology Co., Ltd., Hsinchu (TW)

(72) Inventors: Hao-Jan Mou, Hsinchu (TW); Ching-Sung Lin, Hsinchu (TW); Wen-Yang Yang, Hsinchu (TW); Yung-Lung Han, Hsinchu (TW); Chi-Feng Huang, Hsinchu (TW); Chang-Yen Tsai, Hsinchu (TW); Wei-Ming Lee, Hsinchu (TW)

(73) Assignee: MICROJET TECHNOLOGY CO., LTD., Hsinchu (TW)

( * ) Notice: Subject to any disclaimer, the term of this patent is extended or adjusted under 35 U.S.C. 154(b) by 326 days.

This patent is subject to a terminal disclaimer.

(21) Appl. No.: 17/185,127

(22) Filed: Feb. 25, 2021

(65) Prior Publication Data

US 2021/0275041 A1 Sep. 9, 2021

(30) Foreign Application Priority Data

Mar. 3, 2020 (TW) ................................ 109106974

(51) Int. Cl.
*A61B 5/0235* (2006.01)
*A61B 5/00* (2006.01)
*A61B 5/0225* (2006.01)

(52) U.S. Cl.
CPC .......... *A61B 5/0235* (2013.01); *A61B 5/0004* (2013.01); *A61B 5/0022* (2013.01);
(Continued)

(58) Field of Classification Search
CPC ... A61B 5/0235; A61B 5/0004; A61B 5/0022; A61B 5/0225; A61B 2562/0247; A61B 2562/028
See application file for complete search history.

(56) References Cited

U.S. PATENT DOCUMENTS

| 5,692,512 A | * | 12/1997 | Flachslaender | ...... | A61B 5/0235 |
| | | | | | 600/490 |
| 2018/0289271 A1 | * | 10/2018 | Axelrod | ............... | A61B 5/6824 |

(Continued)

FOREIGN PATENT DOCUMENTS

| TW | I676462 B | 11/2019 |
| TW | M586596 U | 11/2019 |
| TW | I682767 B | 1/2020 |

*Primary Examiner* — Alex M Valvis
*Assistant Examiner* — Jonathan M Haney
(74) *Attorney, Agent, or Firm* — Birch, Stewart, Kolasch & Birch, LLP

(57) ABSTRACT

A blood pressure measurement module is provided and includes a base, a valve plate, a top cover, a micro pump, a driving circuit board and a pressure sensor. The valve plate is disposed between the base and the top cover. The micro pump is disposed within the base. The pressure sensor is disposed on the driving circuit board. An air inlet groove and the pressure sensor are connected to an airbag. The micro pump is actuated to make the airbag be inflated and oppress the skin of a user. The pressure sensor detects the pressure change within the airbag to measure the blood pressure of the user.

18 Claims, 27 Drawing Sheets

(52) U.S. Cl.
CPC ...... *A61B 5/0225* (2013.01); *A61B 2562/028* (2013.01); *A61B 2562/0247* (2013.01)

(56) References Cited

U.S. PATENT DOCUMENTS

| | | | |
|---|---|---|---|
| 2019/0274557 A1* | 9/2019 | Zhou | A61B 5/02241 |
| 2021/0022627 A1* | 1/2021 | Woehrle | A61B 5/02427 |
| 2021/0127987 A1* | 5/2021 | Mou | G01L 19/0007 |

* cited by examiner

BLOOD PRESSURE MEASUREMENT MODULE

FIELD OF THE INVENTION

The present disclosure relates to a blood pressure measurement module, and more particularly to an ultra-thin type blood pressure measurement module combined with a wearable electronic device or a mobile device.

BACKGROUND OF THE INVENTION

In recent years, the awareness of personal health care is gradually risen. Therefore, people hope that their own physical conditions can be measured on a regular basis. However, most of the instruments for measuring the physical conditions are fixed, and almost all people have to go to a fixed medical service station or a hospital. Even through there are several measurement instruments provided for household use, the sizes of those instruments are too large and not easy to carry. In the current society emphasizing rapidity, it is difficult to meet the requirements of users.

Among them, the blood pressure is regarded as the best one to reflect the physical condition and none else. The blood vessels in everyone's body are like the roads all over the body, and the blood pressure is like the road condition. It is possible to understand the state of blood transport by the blood pressure. Therefore, if there is anything happened in the body, it is reflected clearest by the blood pressure.

In view of this, it needs to provide a blood pressure measurement device capable of measuring the blood pressure accurately at any time and being combined with a wearable device or a portable electronic device, so as to allow the user to quickly confirm the blood pressure status anytime, anywhere, and overcome the above-mentioned drawbacks in the prior art.

SUMMARY OF THE INVENTION

An object of the present disclosure is to provide a blood pressure measurement module for combination with a portable electronic device or a wearable electronic device, which is convenient for users to carry, and capable of achieving the blood pressure measurement without being restricted by time and place.

In accordance with an aspect of the present disclosure, a blood pressure measurement module is provided. The blood pressure measurement module includes a base, a valve plate, a top cover, a micro pump, a driving circuit board and a pressure sensor. The base includes a valve-carrying region, an accommodation-slot region, an air inlet and a penetration hole. The valve-carrying region and the accommodation-slot region are disposed on different surfaces, respectively, and the air inlet and the penetration hole are in fluid communication with the accommodation-slot region. A first recessed chamber and a second recessed chamber are formed on the valve-carrying region, a plurality of first through holes pass through and are disposed in the first recessed chamber and in fluid communication with the accommodation-slot region, and a first protrusion protrudes from a center of the first recessed chamber. At least one second through hole passes through and is disposed in the second recessed chamber and in fluid communication with the accommodation-slot region. A gas-collection chamber and a sensor chamber are concavely formed in the accommodation-slot region, the sensor chamber is disposed adjacent to and in fluid communication with one side of the gas-collection chamber, and in fluid communication with the air inlet and the penetration hole. The valve plate is disposed and carried on the valve-carrying region and includes a valve hole. The valve hole is corresponding in position to the first protrusion. The top cover is sealed on the valve-carrying region to cover and seal the valve plate and the penetration hole. The top cover includes an air inlet groove, a discharging outlet and a mounting surface. The air inlet groove and the discharging outlet are spaced apart from each other, the mounting surface correspondingly covers the valve plate, an air inlet chamber is recessed on the mounting surface and in fluid communication with the air inlet groove, and a discharging chamber is recessed on the mounting surface and corresponding in position to the discharging outlet. A second protrusion protrudes from a center of the discharging chamber, and the discharging outlet passes through a center of the second protrusion and is in fluid communication with the discharging chamber, so that the valve plate and the second protrusion abut each other to form a pre-force for closing the discharging outlet. A communication groove is recessed between the air inlet chamber and the discharging chamber, and the air inlet groove is opposed to the mounting surface and in fluid communication with the mounting surface. The air inlet groove includes a connection end and an extension end, the connection end is externally connected to an airbag, and the extension end is opposed to the connection end, extended to and corresponding in position to the penetration hole. The micro pump 4 is disposed in the accommodation-slot region and covering the gas-collection chamber, and includes a cover slot. The driving circuit board covers the accommodation-slot region and provides a driving signal for the micro pump, so as to control operations of the micro pump. The pressure sensor is disposed on and electrically connected to the driving circuit board. The pressure sensor is spatially corresponding to the sensor chamber of the accommodation-slot region of the base, correspondingly passes through the penetration hole, and is sleeved in the cover slot of the top cover, so as to communicate with the air inlet groove and communicate with the airbag. The micro pump is driven by the driving circuit board to achieve a gas transport, gas outside the base is introduced into the accommodation-slot region through the air inlet, and continuously transported and introduced into the gas-collection chamber to concentrate, so as to allow the gas to push the valve plate away from abutting the first protrusion and flow through the valve hole, whereby the gas flowing through the valve hole is continuously transported and introduced into the air inlet groove of the top cover and concentrated in the airbag, the airbag is inflated to oppress skin of a user under measuring, and the user's blood pressure is measured and calculated through the pressure sensor.

The above contents of the present disclosure will become more readily apparent to those ordinarily skilled in the art after reviewing the following detailed description and accompanying drawings, in which:

DETAILED DESCRIPTION OF THE PREFERRED EMBODIMENT

Figure 1A:
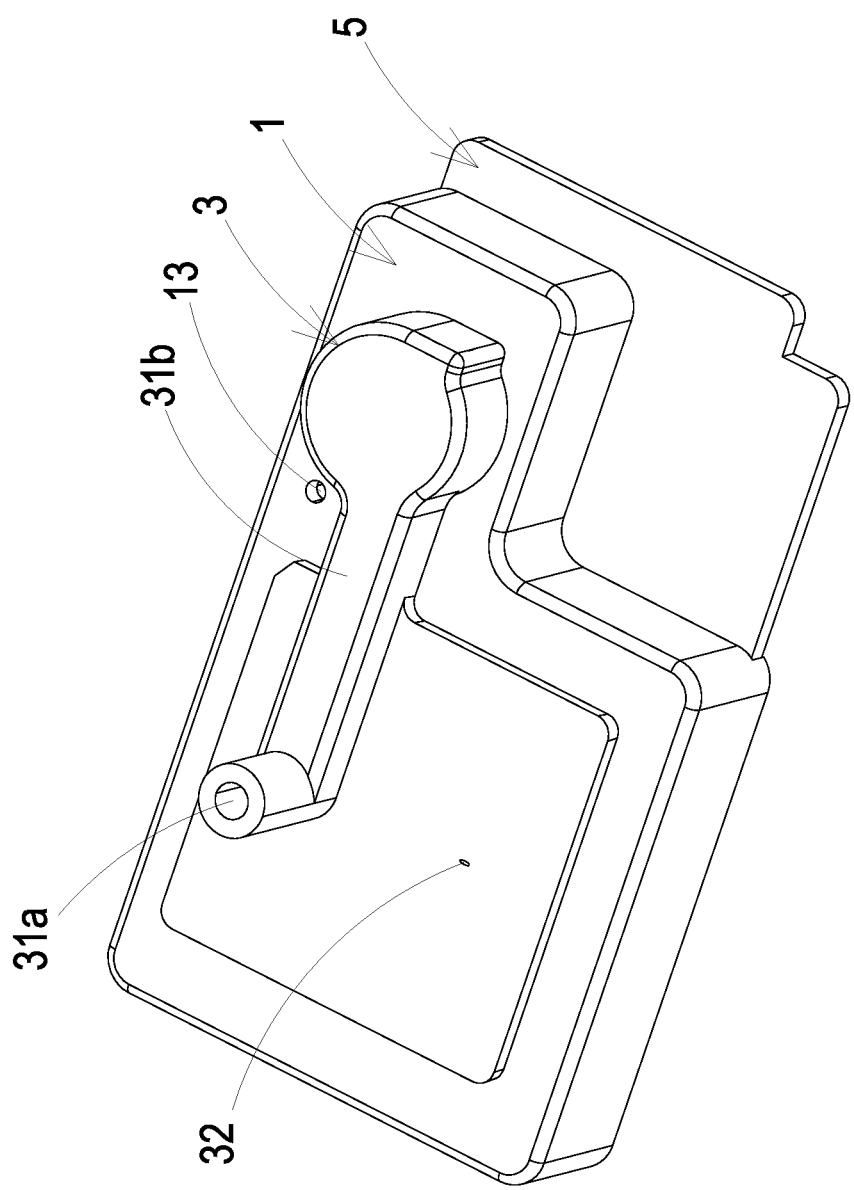
FIG. 1A is a perspective schematic view illustrating a blood pressure measurement module according to a first embodiment of the present disclosure.

The present disclosure will now be described more specifically with reference to the following embodiments. It is to be noted that the following descriptions of preferred embodiments of this disclosure are presented herein for purpose of illustration and description only. It is not intended to be exhaustive or to be limited to the precise form disclosed.

Please refer to FIGS. 1A to 3B. The present discourse provides a blood pressure measurement module including a base 1, a valve plate 2, a top cover 3, a micro pump 4, a driving circuit board 5 and a pressure sensor 6. The base 1 is a frame tank and includes a valve-carrying region 11, an accommodation-slot region 12, an air inlet 13 and a penetration hole 14. The valve-carrying region 11 is disposed on a first surface 1a of the base. The accommodation-slot region 12 is disposed on a second surface 1b of the base 1. The first surface 1a and the second surface 1b are two opposed surfaces, respectively. The air inlet 13 and the penetration hole 14 penetrate from the first surface 1a to the second surface 1b, respectively, and are in fluid communication with the accommodation-slot region 12. In the embodiment, the valve-carrying region 11 includes a first recessed chamber 11a, a plurality of first through holes 11b, a first protrusion 11c and a plurality of protruding posts 11. The first recessed chamber 11a is concavely formed in the valve-carrying region 11. The first protrusion 11c protrudes from a center of the first recessed chamber 11a. The plurality of first through holes 11b surround the first protrusion 11c. Each of the first through holes 11b passes through and is in fluid communication with the accommodation-slot region 12. The plurality of protruding posts 11d are disposed adjacent to the valve-carrying region 11, respectively. In the embodiment, preferably but not exclusively, there are four protruding posts 11d disposed adjacent to the four corners of the valve-carrying region 11, respectively. Moreover, in the embodiment, the valve-carrying region 11 further includes a second recessed chamber 11e and at least one second through hole 11f. The second recessed chamber 11e is spaced apart from the first recessed chamber 11a. The at least one second through hole 11f passes through the second recessed chamber 11e and in fluid communication with the accommodation-slot region 12. In the embodiment, the accommodation-slot region 12 includes a gas-collection chamber 12a and a sensor chamber 12b concavely formed therein. The gas-collection chamber 12a is in fluid communication with the plurality of first through holes 11b and the second through hole 11f. The second through hole 11f is advantageous of increasing a passage between the gas-collection chamber 12a and the valve-carrying region 11, so as to accelerate the speed of transporting the gas in the gas-collection chamber 12a to the valve-carrying region 11. In the embodiment, the sensor chamber 12b is disposed adjacent to and in fluid communication with one side of the gas-collection chamber 12a, and in fluid communication with the air inlet 13 and the penetration hole 14.

Figure 5:
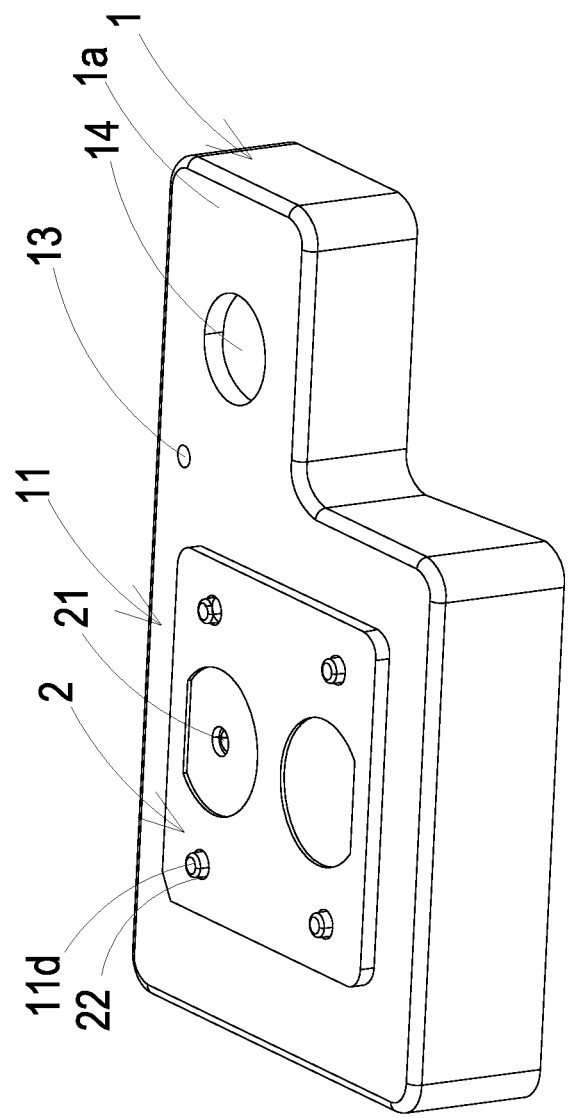
FIG. 5 is a perspective schematic view showing the valve plate of the blood pressure measurement module disposed on the base.

Please refer to FIG. 5. In the embodiment, the valve plate 2 is disposed and carried on the valve-carrying region 11. The valve plate 2 includes a valve hole 21 and a plurality of positioning holes 22. The valve hole 12 is corresponding in position to the first protrusion 11c of the valve-carrying region 11. Preferably but not exclusively, the valve hole 21 vertically corresponds to the first protrusion 11c of the valve-carrying region 11. In the embodiment, the plurality of positioning holes 22 is corresponding to the plurality of protruding posts 11d, respectively, so as to correspondingly sieving the plurality of protruding posts 11d of the valve-carrying region 11, whereby the valve plate 2 is carried and positioned on the valve-carrying region 11 without offset, and it ensures that the valve hole 21 is corresponding in position to the first protrusion 11c.

Figure 10:
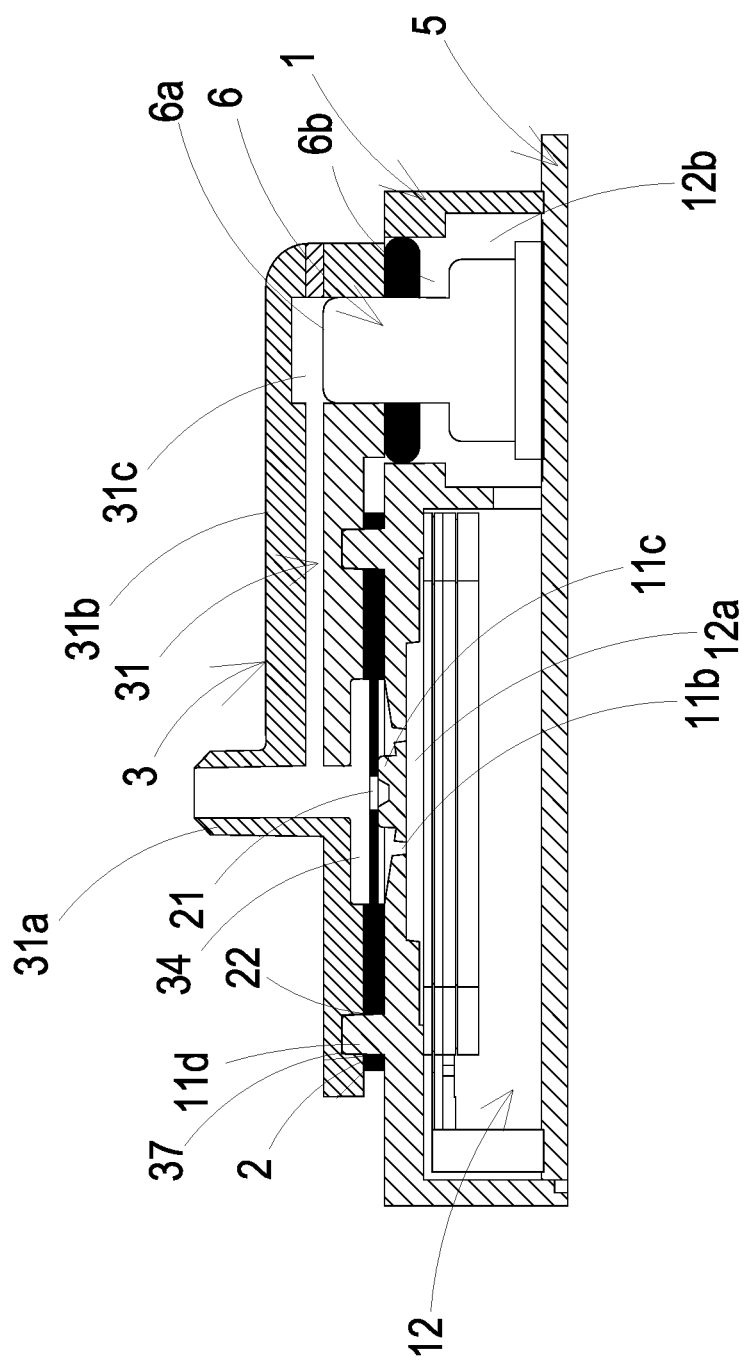
FIG. 10 is a schematic cross-sectional view taken along the line AA in FIG. 1B.
Figure 11:
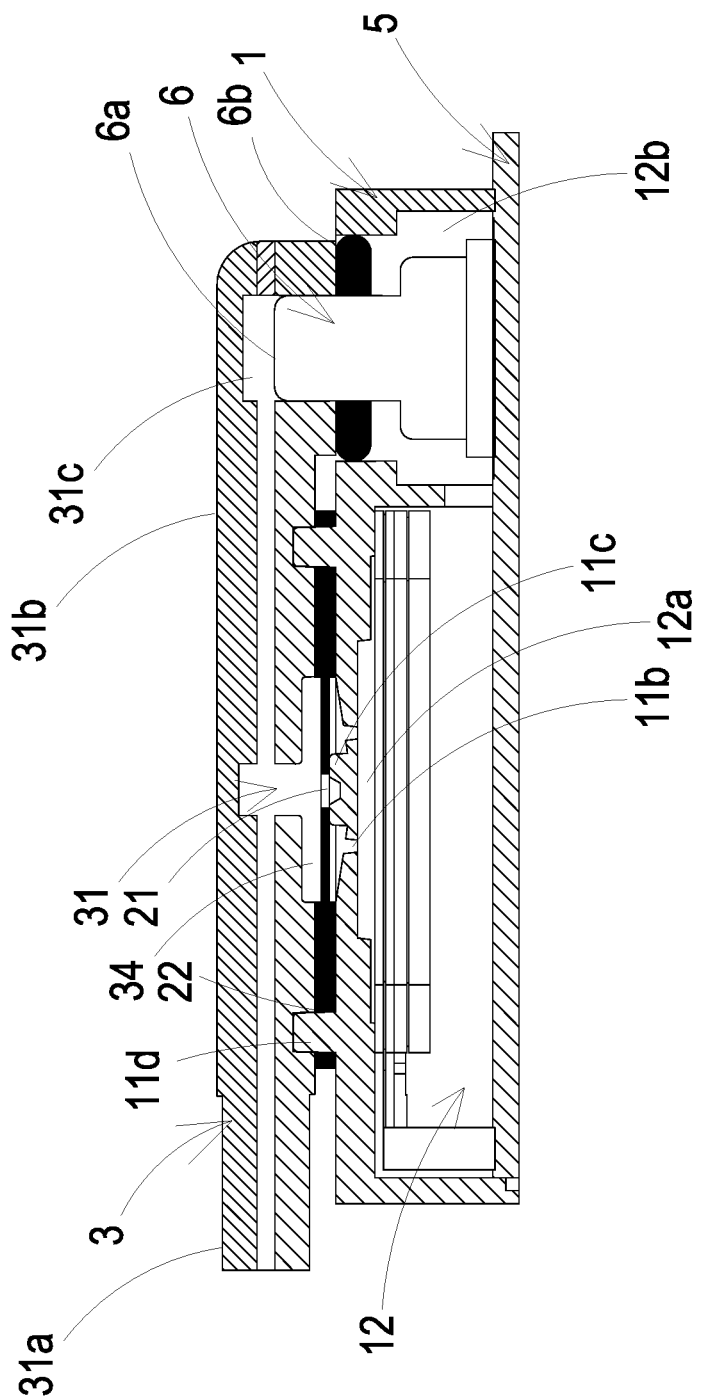
FIG. 11 is a schematic cross-sectional view taken along the line CC in FIG. 2B.

In the embodiment, the top cover 3 is sealed on the valve-carrying region 11 to cover and seal the valve plate 2 and the penetration hole 14. Furthermore, as shown in FIGS. 10 and 11, the top cover 3 includes an air inlet groove 31, a discharging outlet 32 and a mounting surface 33. The air inlet groove 31 and the discharging outlet 32 are spaced apart from each other. The mounting surface 33 correspondingly covers the valve plate 2. Moreover, an air inlet chamber 34 is recessed on the mounting surface 33 and in fluid communication with the air inlet groove 31. In addition, a discharging chamber 35 is recessed on the mounting surface 33 and corresponding in position to the discharging outlet 32. A second protrusion 35a protrudes from a center of the discharging chamber 35, and the discharging outlet 32 passes through a center of the second protrusion 35a and is in fluid communication with the discharging chamber 35, so that the valve plate 2 and the second protrusion 35a abut each other to form a pre-force for closing the discharging outlet 32. In the embodiment, a communication groove 36 is recessed between the air inlet chamber 34 and the discharging chamber 35, so that the air inlet chamber 34 and the discharging chamber 35 are in fluid communication with each other. Moreover, as shown FIG. 3B, FIG. 10 and FIG. 11, the mounting surface 33 of the top cover 3 further includes a plurality mounting-surface positioning holes 37 corresponding to the plurality of protruding posts 11d of the valve-carrying region 11, respectively, so as to correspondingly sieving the plurality of protruding posts 11d of the valve-carrying region 11, whereby, the valve plate 2 is clamped and positioned between the base 1 and the top cover 3 without offset.

Please refer to FIGS. 1A to 3B, again. In the embodiment, the air inlet groove 31 is opposed to the mounting surface 33, runs through from the opposed side and is in fluid communication with the mounting surface 33. In the embodiment, the air inlet groove 31 includes a connection end 31a and an extension end 31b. The connection end 31a is externally connected to an airbag (not shown). In an embodiment, preferably but not exclusively, the connection end 31a of the air inlet groove 31 is externally connected to the airbag in a vertical direction, as shown in FIG. 1A. In another embodiment, preferably but not exclusively, the connection end 31a of the air inlet groove 31 is externally connected to the airbag in a horizontal direction. In the embodiment, another side of the connection end 31a is in fluid communication with air inlet chamber 34 directly, as shown in FIGS. 10 and 11. Moreover, the extension end 31b is opposed to the connection end 31a, extended to and corresponding in position to the penetration hole 14, and includes a cover slot 31c.

Figure 12:
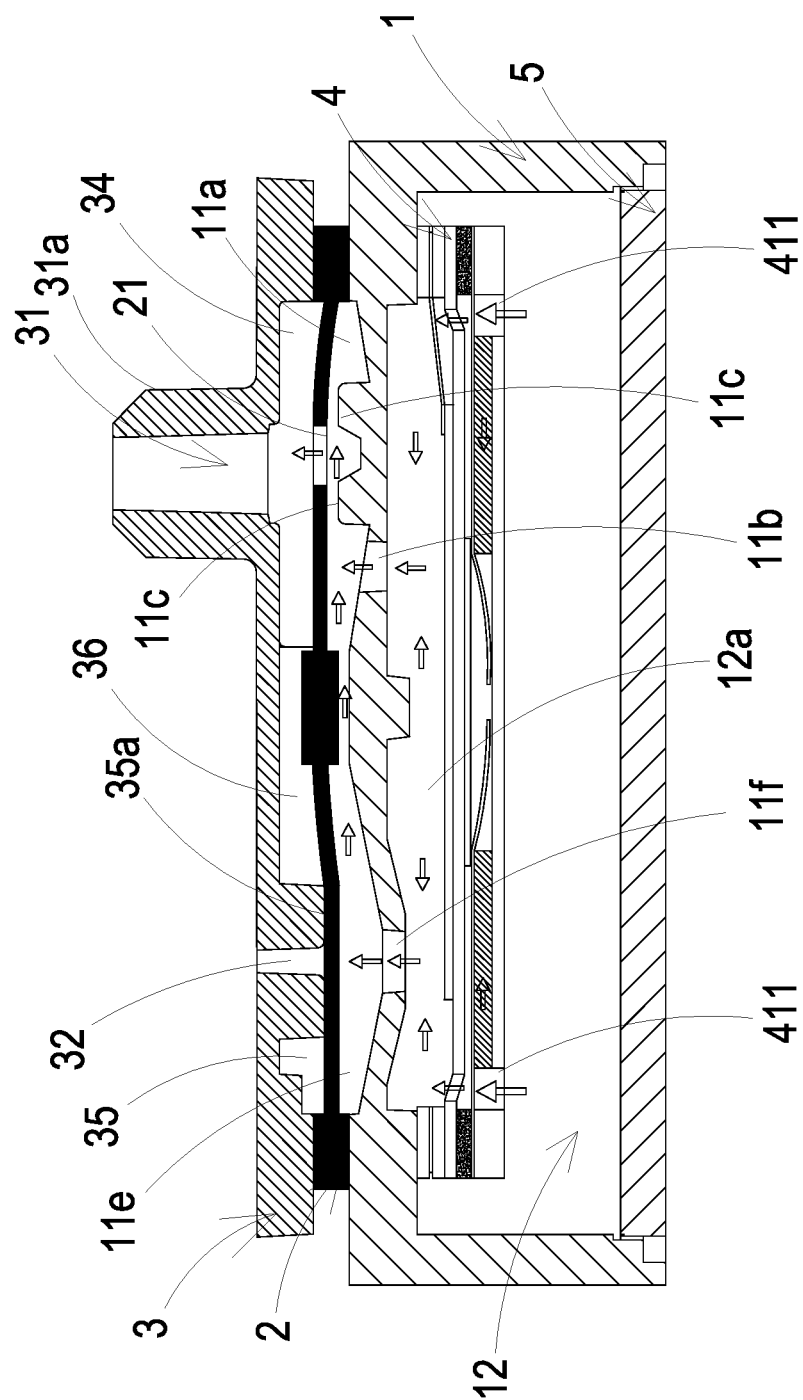
FIG. 12 is a cross-sectional schematic view showing the blood pressure measurement module from the line BB of FIG. 1B performing inflation.

Please refer FIG. 12. In the embodiment, the valve plate 2 is disposed and carried on the valve-carrying region 11. Moreover, the valve plate 2 is carried and positioned on the valve-carrying region 11 without offset. In that, the discharging outlet 32 is located at the center of the second protrusion 35a, and the valve plate 2 and the second protrusion 35a abut each other to close the discharging outlet 32. A pre-force is formed under the normal condition.

Please refer FIGS. 1A to 3B and FIG. 10. In the embodiment, the micro pump 4 is disposed in the accommodation-slot region 12 and covering the gas-collection chamber 12a. In the embodiment, the driving circuit board 5 covers the accommodation-slot region 12 and provides a driving signal for the micro pump 4, so as to control operations of the micro pump 4. Preferably but not exclusively, two conductive pins 4A, 4B of the micro pump 4 are overlapped on two terminal-welding portions 5a, 5b of the driving circuit board 5, respectively, to form the electrical connection and provide the driving signal for controlling the operations of the micro pump 4. Moreover, in the embodiment, the pressure sensor 6 is disposed on and electrically connected to the driving circuit board 5. The pressure sensor 6 includes a detection end 6a disposed on the top. When the driving circuit board covers on the accommodation-slot region 12, the pressure sensor 6 is spatially corresponding to the sensor chamber 12b of the accommodation-slot region 12 of the base 1. Moreover, the detection end 6a correspondingly passes through the penetration hole 14, so that the detection end 6a is sleeved in the cover slot 31c of the top cover 3 and in fluid communication with the air inlet groove 31. Preferably but not exclusively, a sealing element 6b is sleeved on the detection end 6a. When the detection end 6a passes through the penetration hole 14 of the base 1 and is inserted into the air inlet grove 31, the sealing element 6b is helpful for preventing the gas leakage of the air inlet groove 31. In this way, the connection end 31a of the air inlet groove is connected to an airbag, and the detection end 6a of the pressure sensor 6 can detect the gas pressure state in the airbag. In the embodiment, the blood pressure measurement module assembled with the base 1, the valve plate 2, the top cover 3, the micro pump 4, the driving circuit board 5 and the pressure sensor 6 is connected to an airbag. In the embodiment, the micro pump 4 is driven by the driving circuit board 5 to achieve a gas transport. In that, gas outside the base 1 is introduced into the accommodation-slot region 12 through the air inlet 13, and continuously transported and introduced into the gas-collection chamber 12a to concentrate, so as to allow the gas to push the valve plate 2 away from abutting the first protrusion 11c and flow through the valve hole 21. Consequently, the gas flowing through the valve hole 21 is continuously transported and introduced into the air inlet groove 31 of the top cover 3 and concentrated in the airbag, the airbag is inflated to oppress skin of a user under measuring, and the user's blood pressure is measured and calculated through the pressure sensor 6.

From the above descriptions, the blood pressure measurement module of the present disclosure is connected to an airbag to inflate the airbag and oppress the skin of the user. With the pressure sensor 6 detecting the gas pressure state in the airbag, the blood pressure of the user is obtained by calculation and measurement. The detailed features, structures, and operations of the related components in the micro pump of the blood pressure measurement module are further described as follows.

Figure 4:
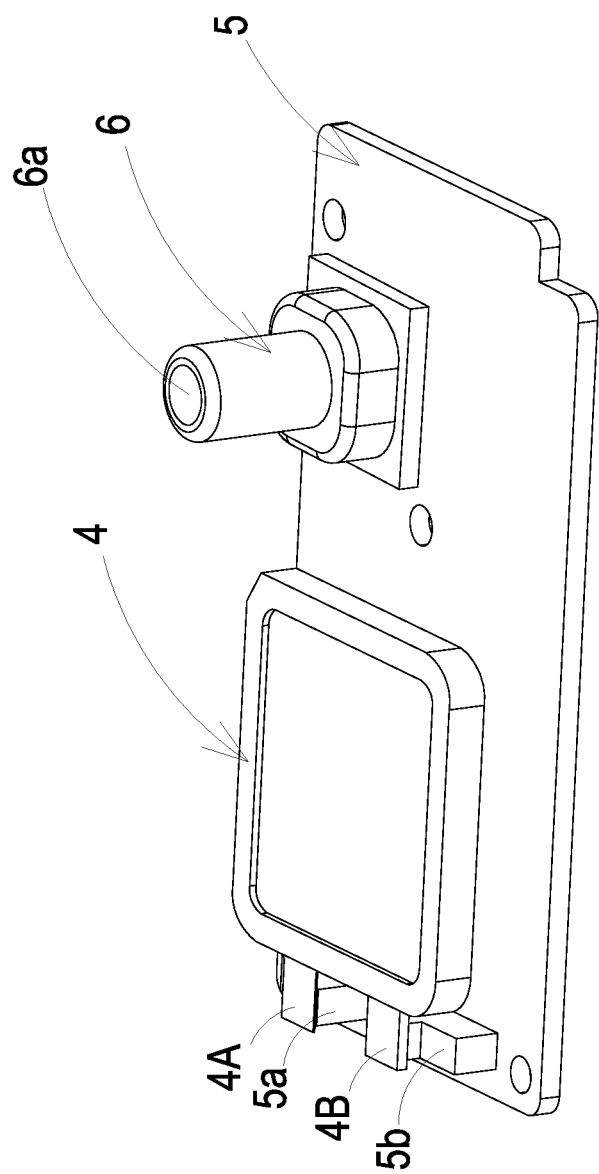
FIG. 4 is a perspective schematic view showing the pressure sensor of the blood pressure measurement module disposed on the driving circuit board.
Figure 6A:
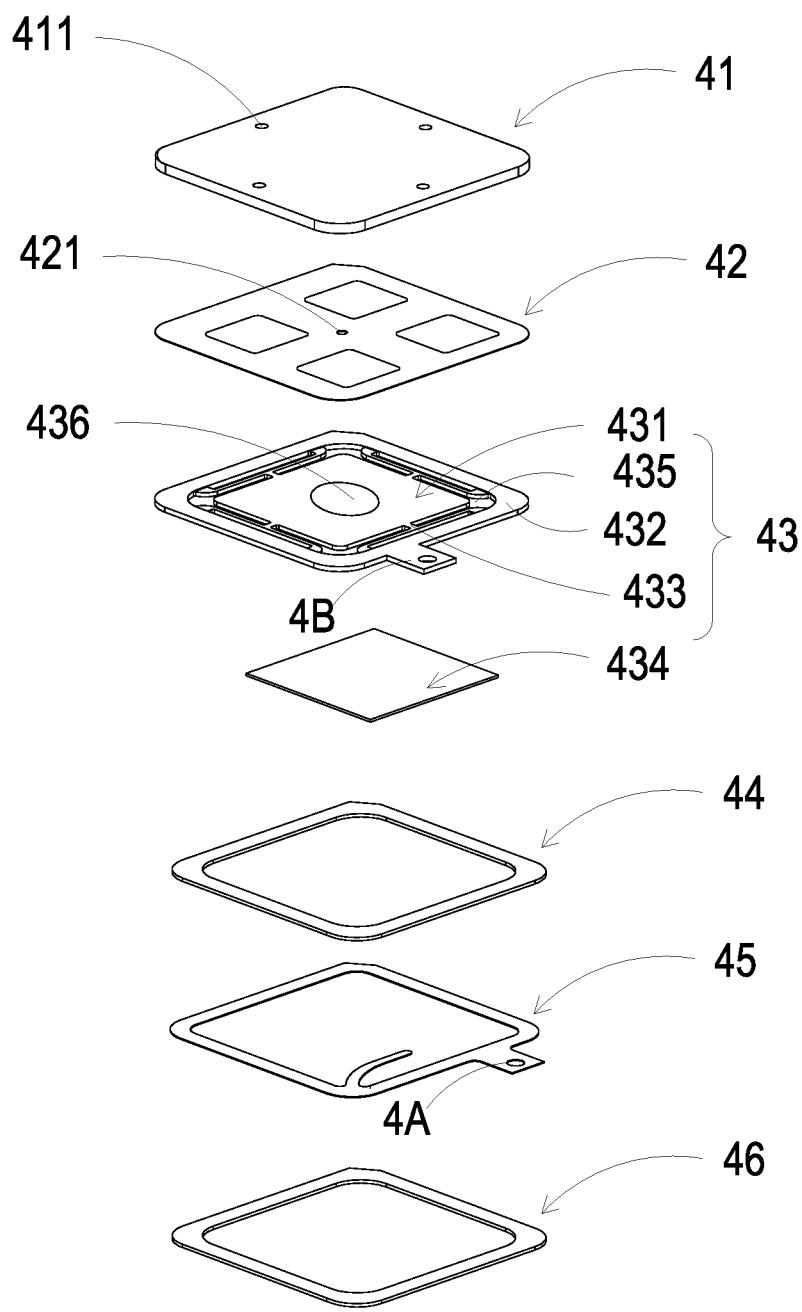
FIG. 6A is an exploded perspective view illustrating the micro pump of the blood pressure measurement module according to the first embodiment of the present disclosure.
Figure 6B:
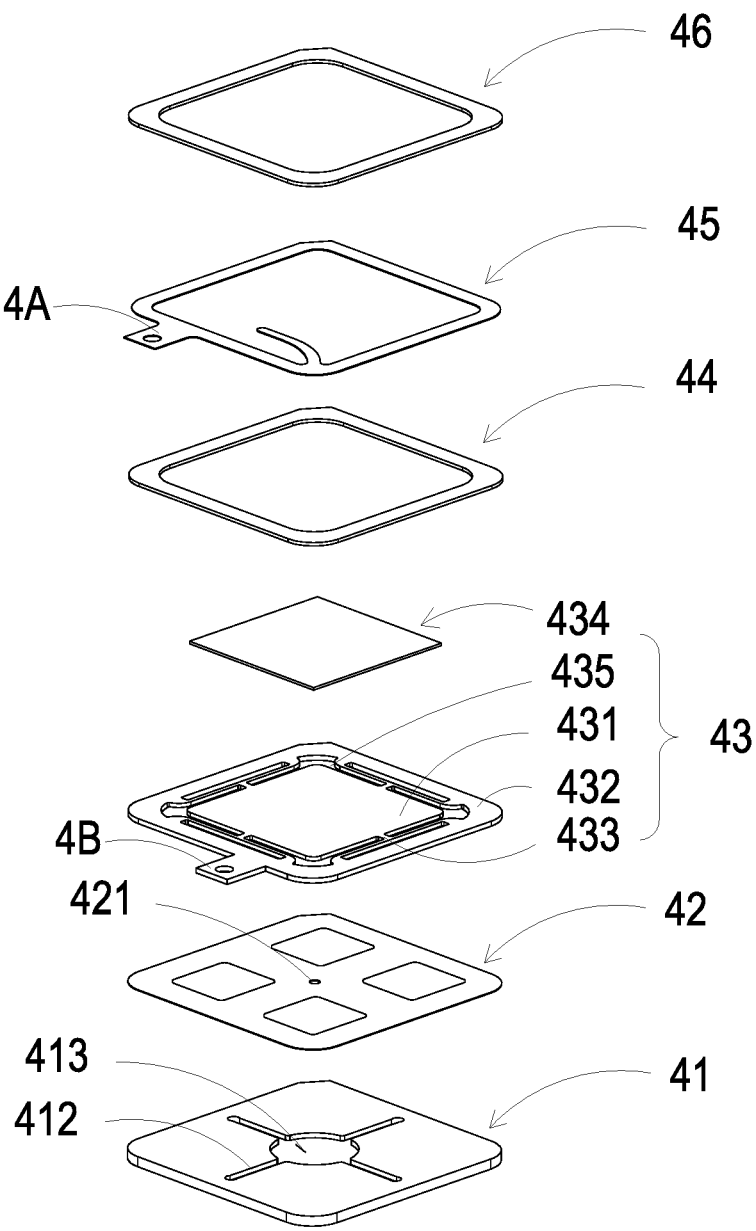
FIG. 6B is an exploded perspective view illustrating the micro pump of the blood pressure measurement module from another view angle according to the first embodiment of the present disclosure.

Please refer to FIG. 6A, FIG. 6B. In the embodiment, the micro pump 4 includes an inlet plate 41, a resonance plate 42, a piezoelectric actuator 43, a first insulating plate 44, a conductive plate 45 and a second insulating plate 46. The piezoelectric actuator 43 is spatially corresponding to the resonance plate 43. The inlet plate 41, the resonance plate 42, the piezoelectric actuator 43, the first insulating plate 44, the conductive plate 45 and the second insulating plate 46 are sequentially stacked. The conductive plate 45 includes a conductive pin 4A protruding and exposed outwardly. The piezoelectric actuator 43 includes a conductive pin 4B protruding and exposed outwardly. As shown in FIG. 4, the conductive pins 4A, 4B are overlapped on the terminal-welding portions 5a, 5b of the driving circuit board 5, respectively to form the electrical connection and provide the driving signal for controlling the operations of the micro pump 4.

In the embodiment, the inlet plate 41 has at least one air intake hole 411, at least one convergence channel 412, and a convergence chamber 413. In this embodiment, the number of the at least one air intake hole 411 is four. The present disclosure is not limited thereto. The at least one air intake hole 411 passes through the inlet plate 41 for allowing gas to flow into the micro pump 4 from the air intake hole 411 in accordance with the action of atmospheric pressure. In this embodiment, the inlet plate 41 includes at least one convergence channel 412. Preferably but not exclusively, the number and the position of the convergence channels 412 are corresponding to the number and the position of the air intake holes 411 disposed on another surface of the inlet plate 41. In the embodiment, the inlet plate 41 includes four air intake holes 411 and four corresponding convergence channels 412, but not limited thereto. Preferably but not exclusively, the convergence chamber 413 is located at the center of the inlet plate 41. In the embedment, first ends of the four convergence channels 412 are in fluid communication with the corresponding air intake holes 411, and second ends of the four convergence channels 412 are in fluid communication with the convergence chamber 413 located at the center of the inlet plate 41. Thus, the gas is inhaled into the convergence channels 412 through the air intake holes 411, and converged to the convergence chamber 413. In the embodiment, the air intake holes 411, the convergence channels 412 and the convergence chamber 413 are integrally formed into one piece.

In some embodiments, preferably but not exclusively, the inlet plate 41 is made of stainless steel. In other embodiments, the depth of the convergence chamber 413 is the same as the depth of the convergence channels 412, but the present disclosure is not limited thereto.

In the embodiment, the resonance plate 42 is made of a flexible material, but not limited thereto. In the embodiment, the resonance plate 42 has a central aperture 421 corresponding in position to the convergence chamber 413 of the inlet plate 41 for the gas flowing therethrough. In other embodiments, the resonance plate 42 is made of a copper material, but it is not limited thereto.

In the embodiment, the piezoelectric actuator 43 includes a suspension plate 431, an outer frame 432, at least one bracket 433 and a piezoelectric element 434. Moreover, the piezoelectric actuator 43 includes a conductive pin 4B. The suspension plate 431 is square-shaped and permitted to undergo a bending vibration. The outer frame 432 surrounds the suspension plate 431. The at least one bracket 433 is connected between the suspension plate 431 and the outer frame 432 for providing an elastic support. In the embodiment, the piezoelectric element 434 is square-shaped and attached on a surface of the suspension plate 431. When a voltage is applied to the piezoelectric element 434, the suspension plate 431 is driven to undergo the bending vibration. Preferably but not exclusively, the piezoelectric element 434 has a side, and a length of the side of the piezoelectric element 434 is less than or equal to that of the suspension plate 431. In the embodiment, a plurality of vacant spaces 435 is formed among the suspension plate 431, the outer frame 432 and the at least one bracket 433 and disposed for allowing the gas to pass through the vacant spaces 435. In addition, the piezoelectric actuator 43 further includes a bulge 436. The bulge 435 is disposed on the other surface of the suspension plate 431 that is opposite to the piezoelectric element 434. In the embodiment, the bulge 23ƒ and the piezoelectric element 434 are correspondingly disposed on two opposed surfaces of the suspension plate 431.

Figure 7A:
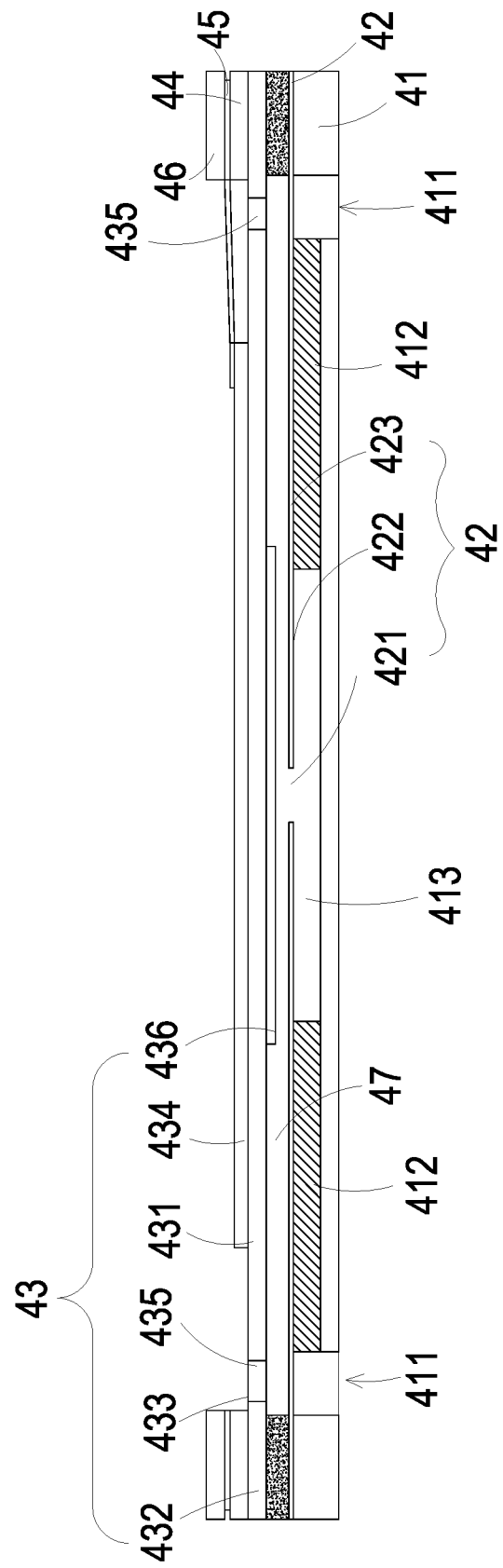
FIG. 7A is a cross-sectional view illustrating the micro pump of the blood pressure measurement module according to the first embodiment of the present disclosure.

Please refer to FIG. 7A. In the embodiment, the inlet plate 41, the resonance plate 42, the piezoelectric actuator 43, the first insulation plate 44, the conductive plate 45 and the second insulation plate 46 are stacked sequentially. The suspension plate 431 of the piezoelectric actuator 43 has a thickness less than that of the outer frame 432. When the resonance plate 43 is stacked on the piezoelectric actuator 43, a chamber space 47 is formed between the suspension plate 431 and the outer frame 432 of the piezoelectric actuator 43 and the resonance plate 42.

Figure 7B:
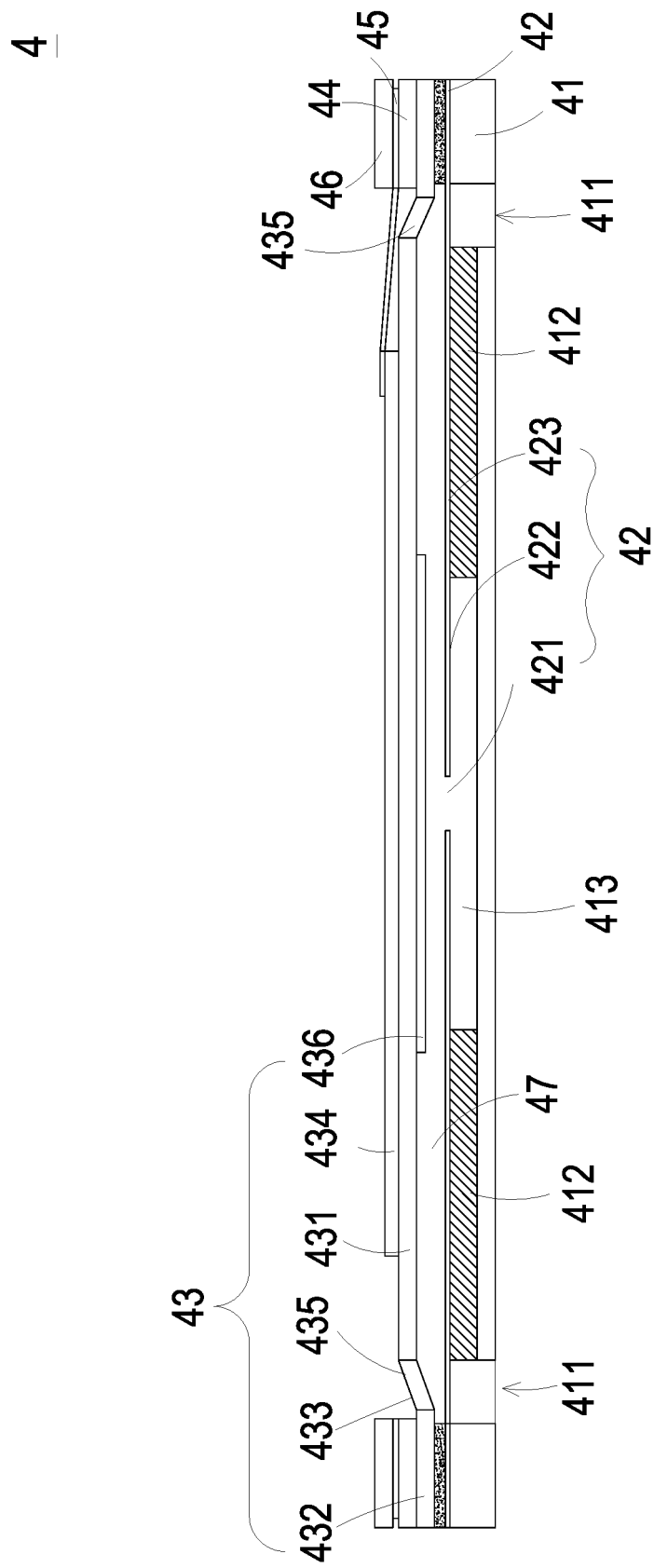
FIG. 7B is a cross-sectional view illustrating the micro pump of the blood pressure measurement module according to the second embodiment of the present disclosure.

Please refer to FIG. 7B. FIG. 7B illustrates a micro pump 4 according to the second embodiment. The components are the same as those in the previous embodiment (FIG. 7A), and not redundantly described herein. Different from the previous embodiment, in the embodiment, the suspension plate 431 of the piezoelectric actuator 43 is formed by stamping to make it extend at a distance in a direction away from the resonance plate 42 when the piezoelectric actuator 43 is not activated. The suspension plate 431 is not at the same level with the outer frame 432. The extended distance can be adjusted through the at least one bracket 433 formed between the suspension plate 431 and the outer frame 432. The bracket 433 and the suspension plate 431 are non-coplanar, so that the piezoelectric actuator 43 has a convex structure.

Figure 7C:
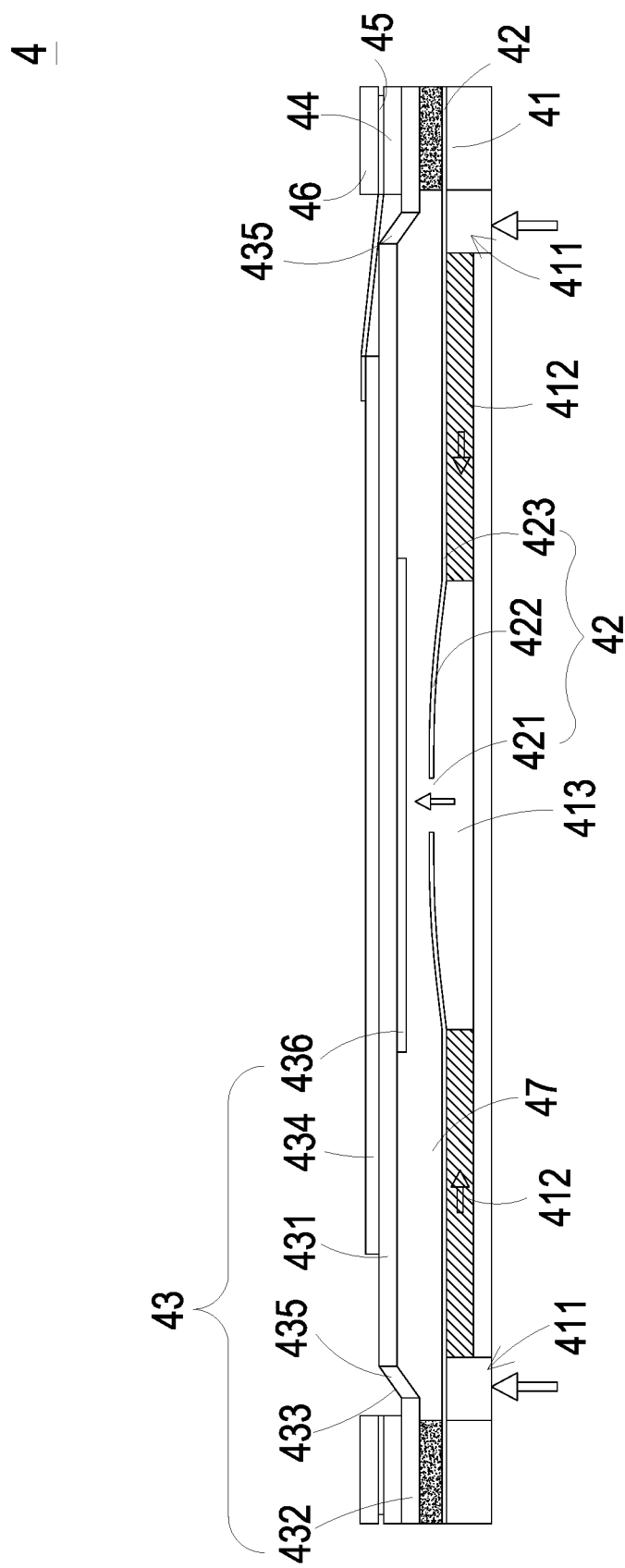
FIGS. 7C to 7E are cross-sectional views illustrating the actions of the micro pump according to the first embodiment of the present disclosure.
Figure 7D:
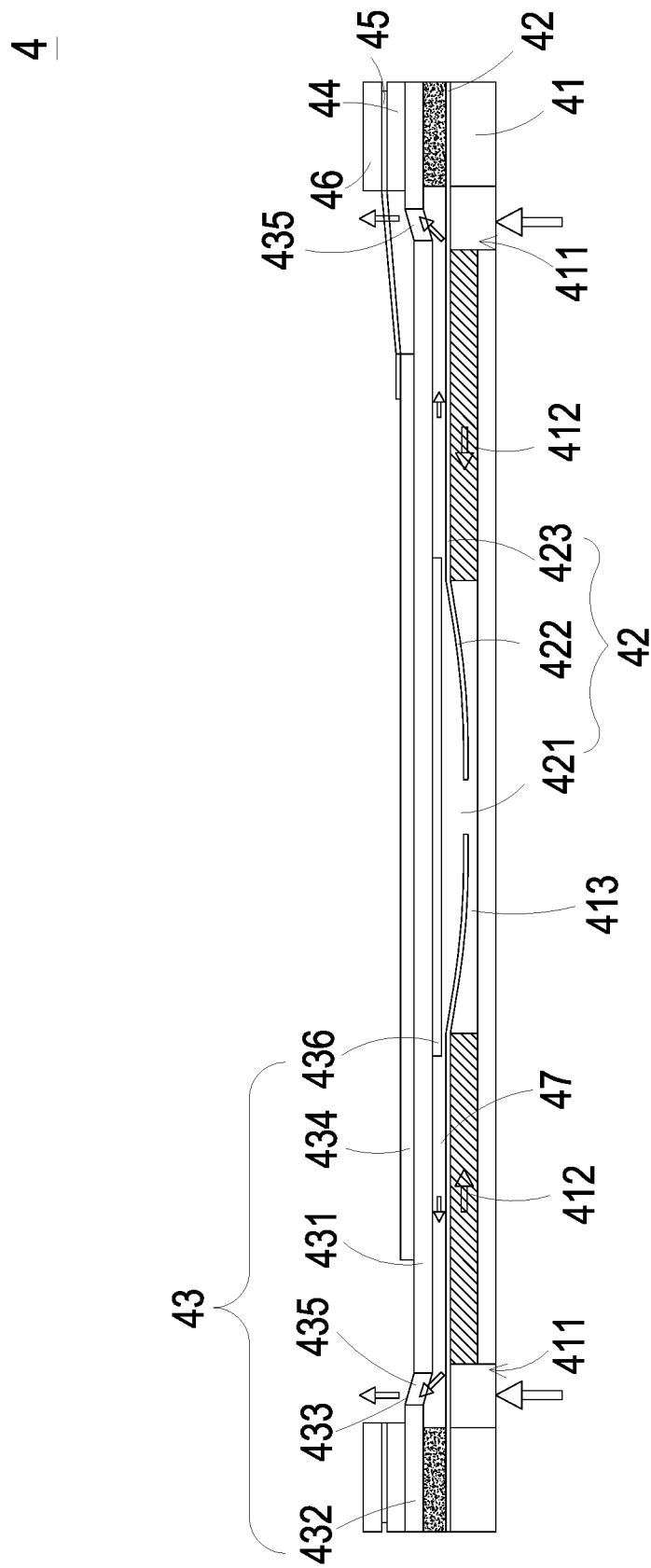
Figure 7E:
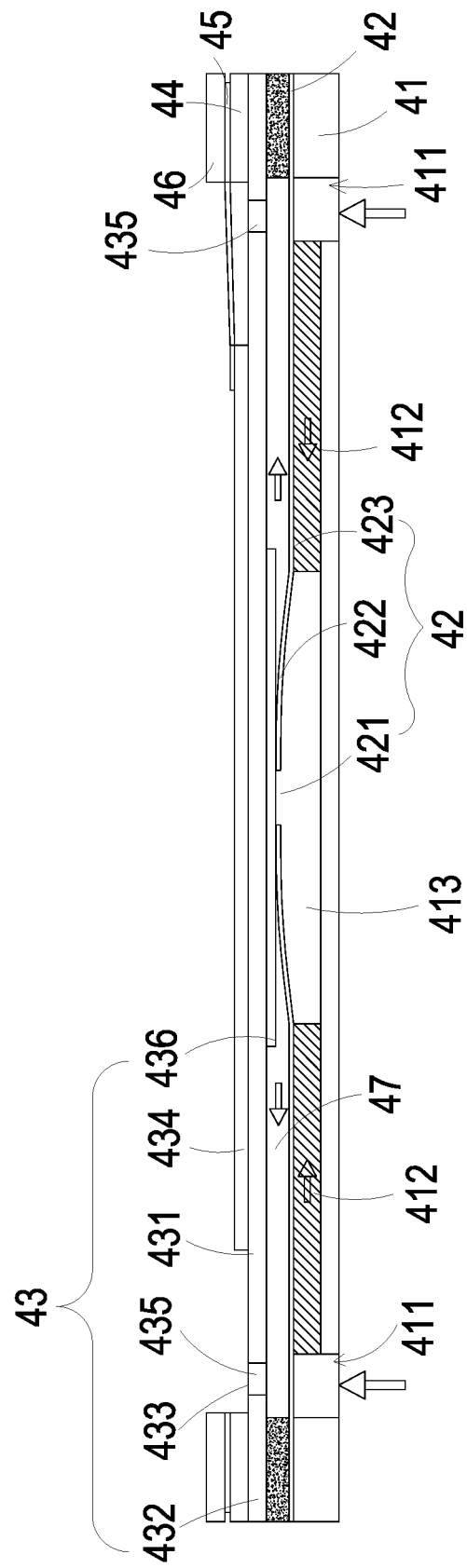

In order to understand the actuations of the gas transportation device 2, please refer to FIGS. 7C to 7E. Firstly, please refer to FIG. 7C, when the piezoelectric element 434 of the piezoelectric actuator 43 is deformed in response to an applied voltage, the suspension plate 431 is driven to displace in the direction away from the resonance plate 42. In that, the volume of the chamber space 47 is increased, a negative pressure is formed in the chamber space 47, and the gas in the convergence chamber 413 is introduced into the chamber space 47. At the same time, the resonance plate 42 is in resonance and is thus displaced synchronously. Thereby, the volume of the convergence chamber 413 is increased. Since the gas in the convergence chamber 413 is introduced into the chamber space 47, the convergence chamber 413 is also in a negative pressure state, and the gas is sucked into the convergence chamber 413 through the air intake holes 411 and the convergence channels 412. Then, as shown in FIG. 7D, the piezoelectric element 434 drives the suspension plate 431 to displace toward the resonance plate 42 to compress the chamber space 47. Similarly, the resonance plate 42 is actuated in resonance to the suspension plate 431 and is displaced. Thus, the gas in the chamber space 47 is further transported to pass through the vacant spaces 435 and discharged out of the micro pump 4. Finally, as shown in FIG. 7E, when the suspension plate 431 is driven by the piezoelectric element 434 to move downwardly and compress the chamber space 47. Similarly, the resonance plate 42 is displaced downwardly by the suspension plate 431 due to resonance. In that, the resonance plate 42 pushes the gas in the chamber space 47 to the vacant spaces 435, and the volume of the convergence chamber 413 is increased. Thus, the gas can continuously pass through the air intake holes 411 and the convergence channels 412, and can be converged in the convergence chamber 413. By repeating the actuations illustrated in FIGS. 7C to 7E continuously, the micro pump 4 can continuously transport the gas at high speed. The gas enters the air intake hole 411, flows through a flow path formed by the inlet plate 41 and the resonance plate 42 with a pressure gradient, and then is transported upwardly through the vacant spaces 435. It achieves the gas transporting operation of the micro pump 4.

Figure 8A:
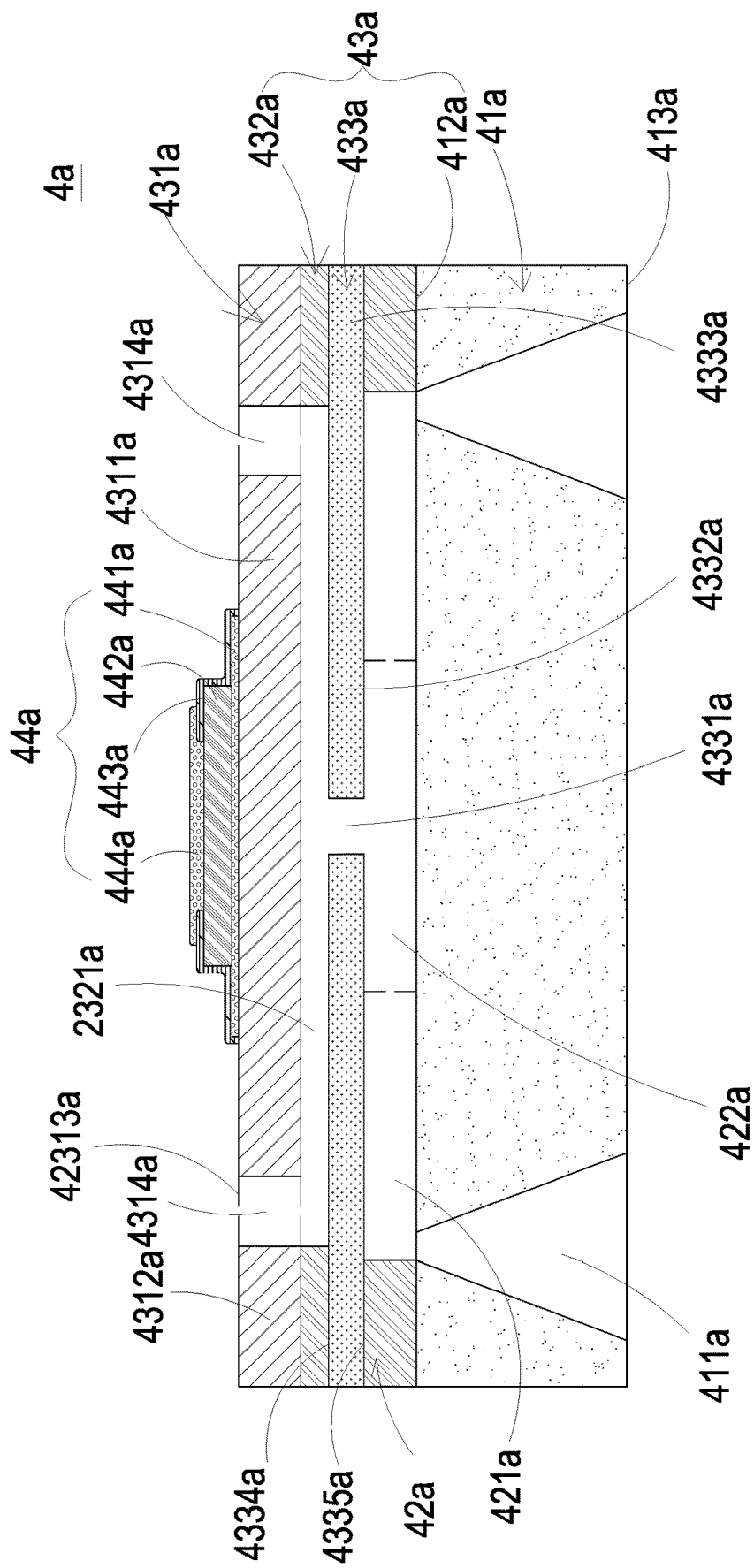
FIG. 8A is a schematic cross-sectional view illustrating a MEMS pump.
Figure 8B:
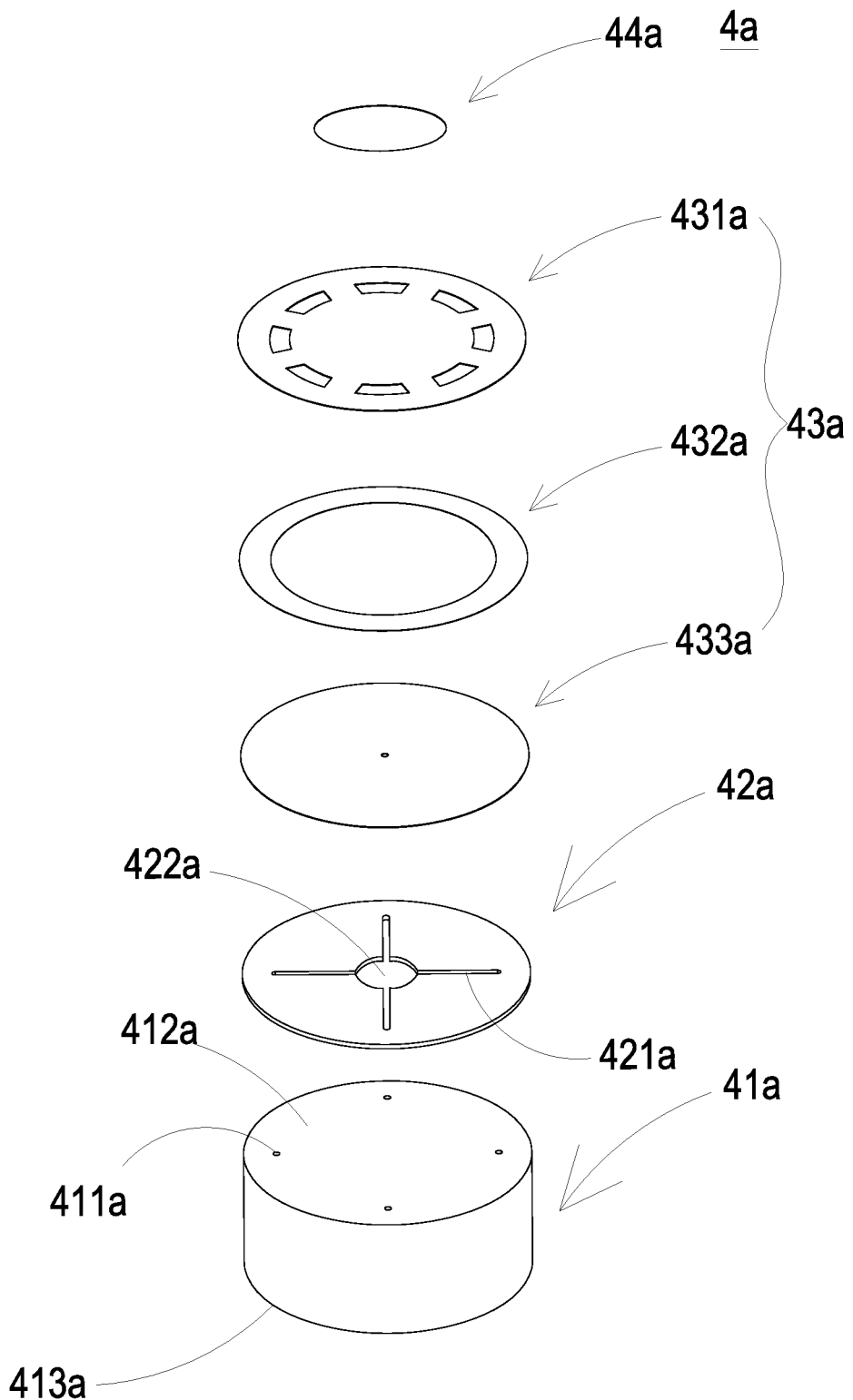
FIG. 8B is a schematic exploded view illustrating the MEMS pump.

In addition, the micro pump 4 in the above embodiment is replaced with a microelectromechanical systems (MEMS) pump 4*a* in another embodiment. Please refer to FIG. 8A and FIG. 8B. The MEMS pump 4*a* includes a first substrate 41*a*, a first oxidation layer 44*a*, a second substrate 43*a* and a piezoelectric component 44*a*. In the embodiment, MEMS pump 4*a* is integrally formed through the processes of epitaxy, deposition, lithography and etching in the semiconductor manufacturing process. It should not be disassembled. In order to detail its internal structure, it is shown in the schematic exploded view of FIG. 8B.

In the embodiment, the first substrate 41a is a Si wafer and has a thickness ranging from 150 μm to 400 μm. The first substrate 41a includes a plurality of inlet apertures 411a, a first surface 412a and a second surface 413a. In the embodiment, there are four inlet apertures 411a, but the present disclosure is not limited thereto. Each inlet aperture 411a penetrates from the second surface 413a to the first surface 412a. In order to improve the inlet-inflow effect, the plurality of inlet apertures 411a are tapered-shaped, and the size is decreased from the second surface 413a to the first surface 412a.

In the embodiment, the first oxidation layer 42a is a silicon dioxide ($SiO_2$) thin film and has the thickness ranging from 10 μm to 20 μm. The first oxidation layer 42a is stacked on the first surface 412a of the first substrate 41a. The first oxidation layer 42a includes a plurality of convergence channels 421a and a convergence chamber 422a. The numbers and the arrangements of the convergence channels 421a and the inlet apertures 411a of the first substrate 41a are corresponding to each other. In the embodiment, there are four convergence channels 421a. First ends of the four convergence channels 421a are in fluid communication with the four inlet apertures 411a of the first substrate 41a, and second ends of the four convergence channels 421a are in fluid communication with the convergence chamber 422a. Thus, after the gas is inhaled through the inlet apertures 411a, the gas flows through the corresponding convergence channels 421a and is converged into the convergence chamber 422a.

In the embodiment, the second substrate 43a is a silicon on insulator (SOI) wafer, and includes a silicon chip layer 431a, a second oxidization layer 432a and a silicon material layer 433a. The silicon chip layer 431a has a thickness ranging from 10 μm to 20 μm, and includes an actuating portion 4311a, an outer peripheral portion 4312a, a plurality of connecting portions 4313a and a plurality of fluid channels 4314a. The actuating portion 4311a is in a circular shape. The outer peripheral portion 4312a is in a hollow ring shape and disposed around the actuating portion 4311a. The plurality of connecting portions 4313a are connected between the actuating portion 4311a and the outer peripheral portion 4312a, respectively, so as to connect the actuating portion 4311a and the outer peripheral portion 4312a for elastically supporting. The plurality of fluid channels 4314a are disposed around the actuating portion 4311a and located between the connecting portions 4313a.

In the embodiment, the second oxidation layer 432a is a silicon monoxide (SiO) layer and has a thickness ranging from 0.5 μm to 2 μm. The second oxidation layer 432a is formed on the silicon chip layer 431a and in a hollow ring shape. A vibration chamber 4321a is collaboratively defined by the second oxidation layer 432a and the silicon chip layer 431a. The silicon material layer 433a is in a circular shape, disposed on the second oxidation layer 432a and bonded to the first oxidation layer 42a. The silicon material layer 433a is a silicon dioxide ($SiO_2$) thin film and has a thickness ranging from 2 μm to 5 μm. In the embodiment, the silicon material layer 423a includes a through hole 4331a, a vibration portion 4332a, a fixing portion 4333a, a third surface 4334a and a fourth surface 4335a. The through hole 4331a is formed at a center of the silicon material layer 433a. The vibration portion 4332a is disposed around the through hole 4331a and vertically corresponds to the vibration chamber 4321a. The fixing portion 4333a is disposed around the vibration portion 4332a and located at a peripheral region of the silicon material layer 433a. The silicon material layer 433a is fixed on the second oxidation layer 432a through the fixing portion 4333a. The third surface 4334a is connected to the second oxidation layer 432a. The fourth surface 4335a is connected to the first oxidation layer 42a. The piezoelectric component 44a is stacked on the actuating portion 4311a of the silicon chip layer 431a.

In the embodiment, the piezoelectric component 44a includes a lower electrode layer 441a, a piezoelectric layer 442a, an insulation layer 443a and an upper electrode layer 444a. The lower electrode 441a is stacked on the actuating portion 4311a of the silicon chip layer 431a. The piezoelectric layer 442a is stacked on the lower electrode layer 441a. The piezoelectric layer 442a and the lower electrode layer 441a are electrically connected through the contact area thereof. In addition, the width of the piezoelectric layer 442a is less than the width of the lower electrode layer 441a, so that the lower electrode layer 441a is not completely covered by the piezoelectric layer 442a. The insulation layer 443a is stacked on a partial surface of the piezoelectric layer 442a and a partial surface of the lower electrode layer 441a, which is uncovered by the piezoelectric layer 442a. The upper electrode layer 444a is stacked on the insulation layer 443a and a remaining surface of the piezoelectric layer 442a without the insulation layer 443a disposed thereon, so that the upper electrode layer 444a is contacted and electrically connected with the piezoelectric layer 442a. At the same time, the insulation layer 443a is used for insulation between the upper electrode layer 444a and the lower electrode layer 441a, so as to avoid the short circuit caused by direct contact between the upper electrode layer 444a and the lower electrode layer 441a.

Figure 9A:
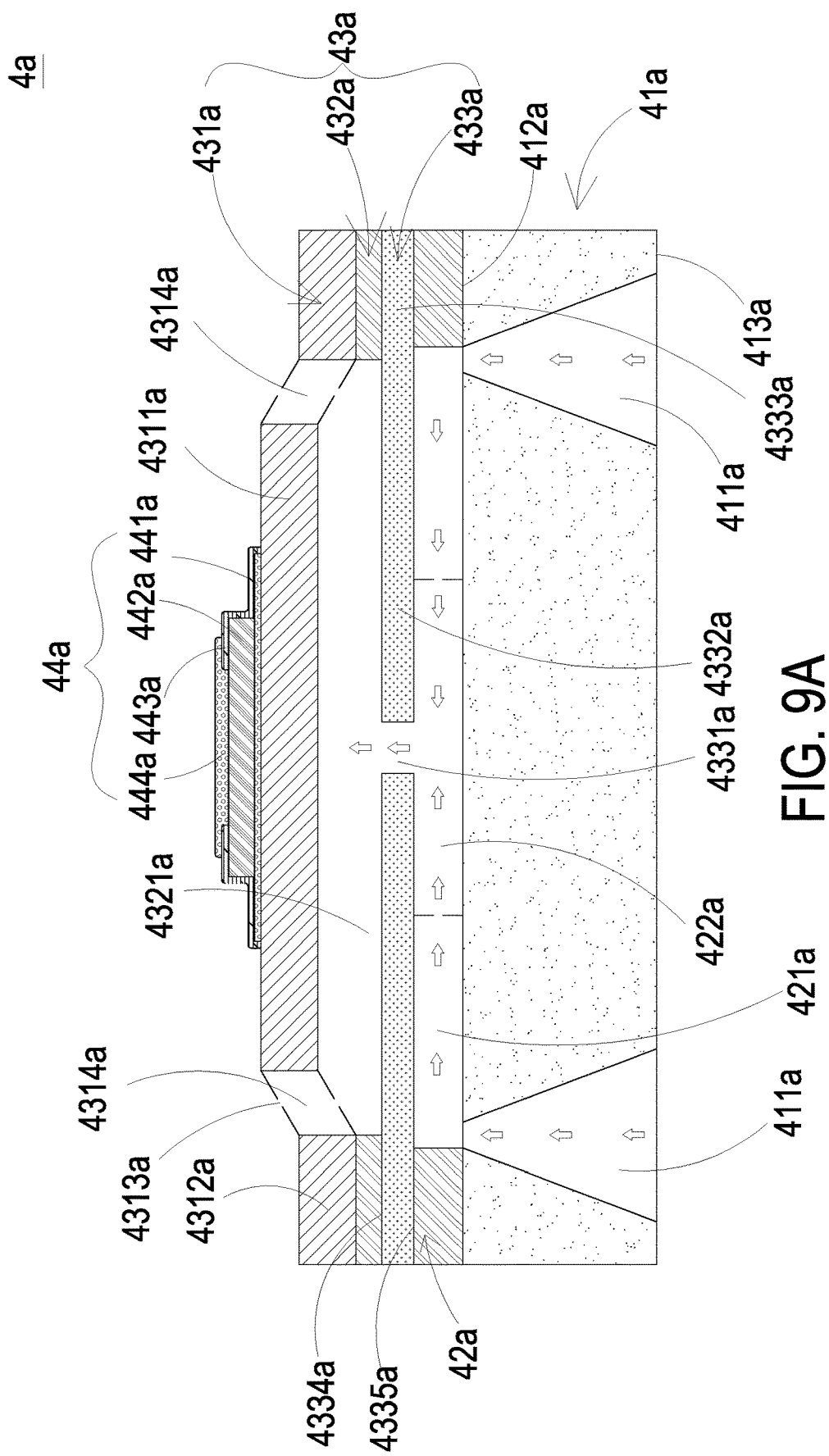
FIGS. 9A to 9C schematically illustrate the actions of the MEMS pump.
Figure 9B:
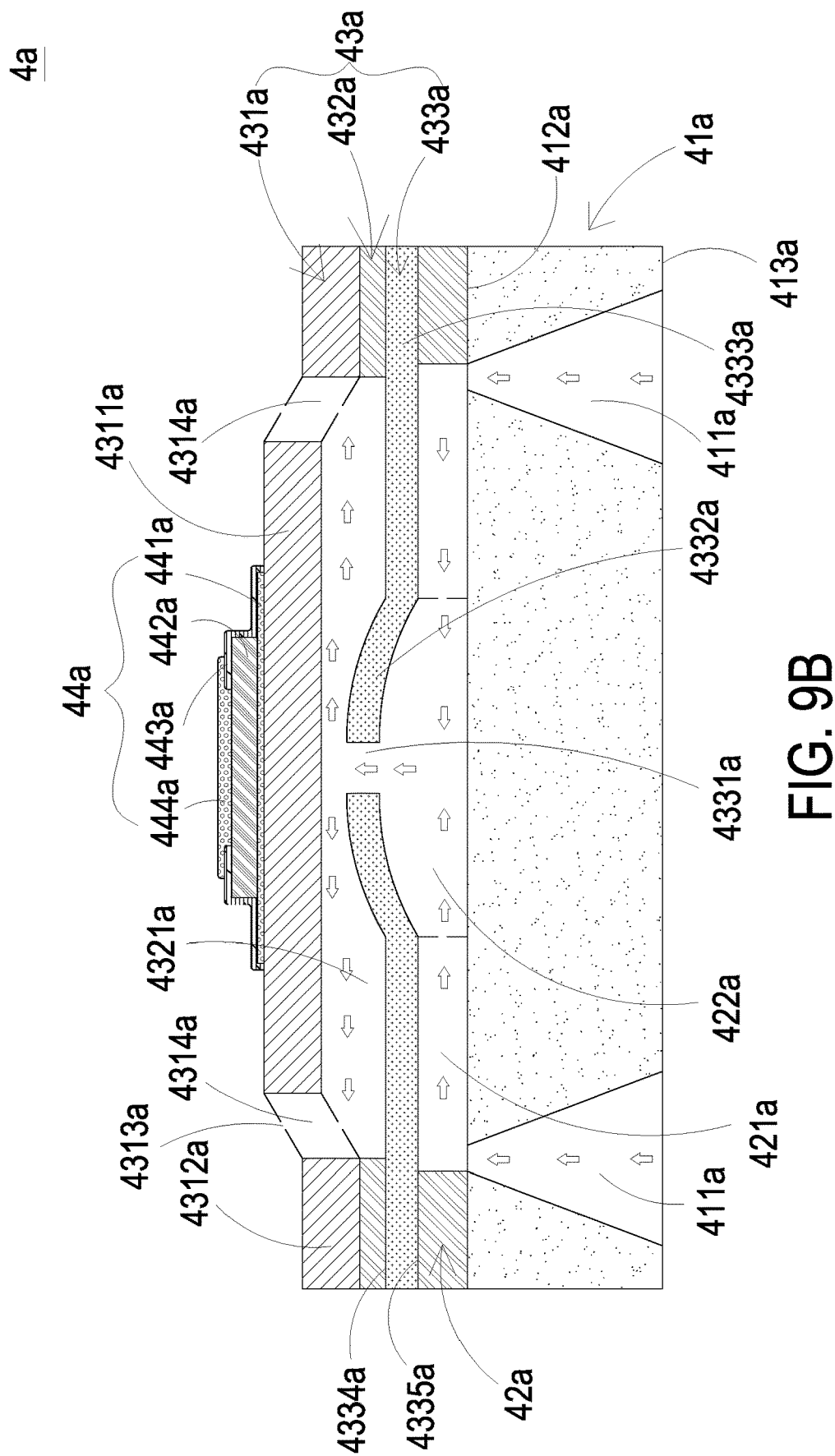
Figure 9C:
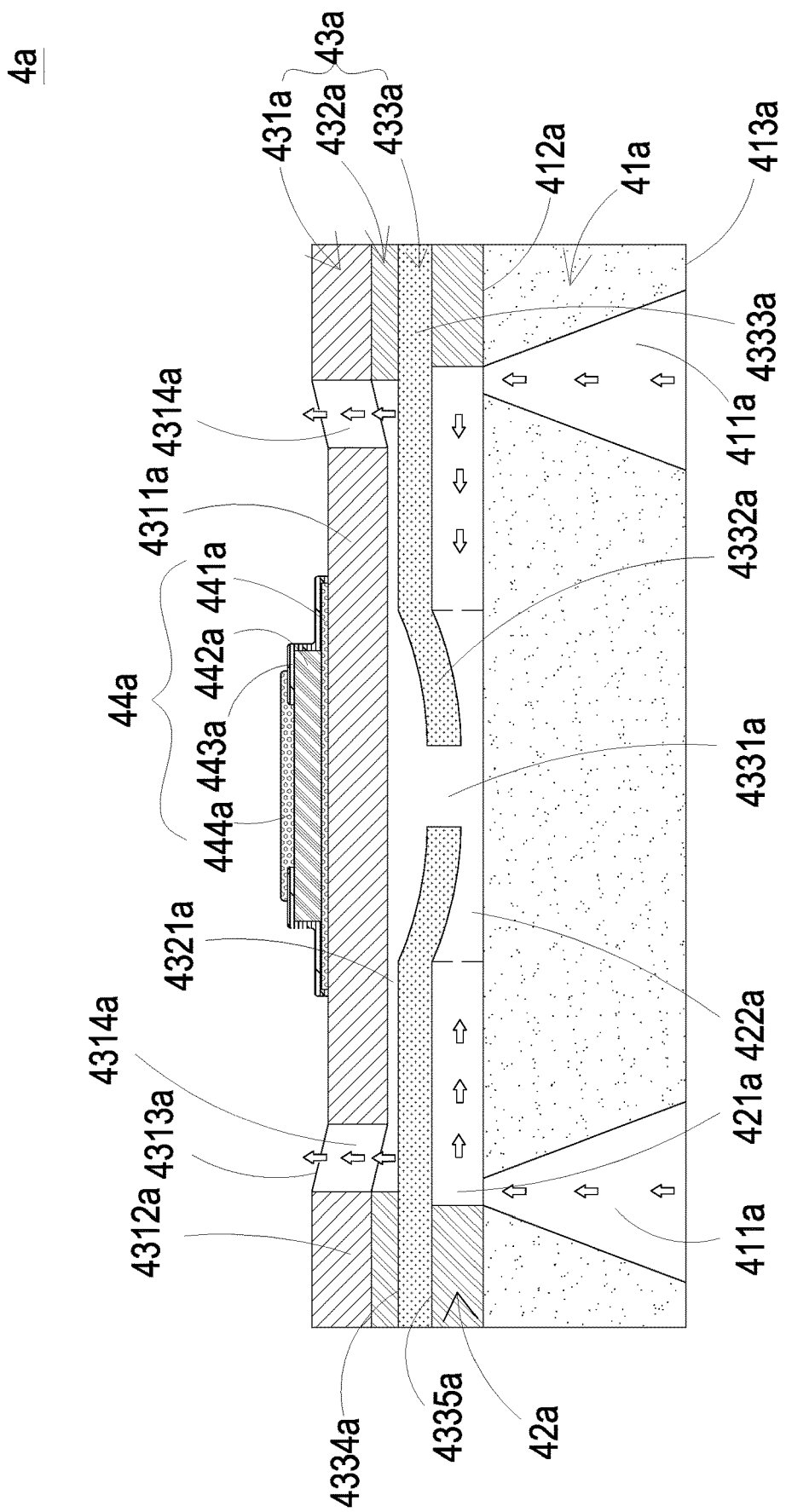

Please refer to FIGS. 9A to 9C. FIGS. 9A to 9C schematically illustrate the actions of the MEMS pump. As shown in FIG. 9A, a driving voltage and a driving signal (not shown) transmitted from the driving circuit board 5 are received by the lower electrode layer 441a and the upper electrode layer 444a of the piezoelectric component 44a, and further transmitted to the piezoelectric layer 442a. After the piezoelectric layer 442a receives the driving voltage and the driving signal, the deformation of the piezoelectric layer 442a is generated due to the influence of the reverse piezoelectric effect. In that, the actuating portion 4311a of the silicon chip layer 431a is driven to displace. When the piezoelectric component 44a drives the actuating portion 4311a to move upwardly, the actuating portion 4311a is separated away from the second oxidation layer 432a to increase the distance therebetween. In that, the volume of the vibration chamber 4321a of the second oxidation layer 432a is expended rapidly, the internal pressure of the vibration chamber 4321a is decreased to form a negative pressure, and the gas in the convergence chamber 422a of the first oxidation layer 42a is inhaled into the vibration chamber 4321a through the through hole 4331a. Further as shown in FIG. 11B, when the actuating portion 4311a is driven by the piezoelectric component 44a to move upwardly, the vibration portion 4332a of the silicon material layer 433a is moved upwardly due to the influence of the resonance principle. When the vibration portion 4332a is displaced upwardly, the space of the vibration chamber 4321a is compressed and the gas in the vibration chamber 4321a is pushed to move to the fluid channels 4314a of the silicon chip layer 431a. In that, the gas flows upwardly through the fluid channel 4314a and is discharged out. Moreover, when the vibration portion 4332a is displaced upwardly to compress the vibration chamber 4321a, the volume of the convergence chamber 422a is expended due to the displacement of the vibration portion 4332a, the internal pressure of the convergence chamber 422a is decreased to form a negative pressure, and the gas outside the MEMS pump 4a is inhaled into the convergence chamber 422a through the inlet apertures 411a. As shown in FIG. 9C, when the piezoelectric component 44a is enabled to drive the actuating portion 4311a of the silicon chip layer 431a to displace downwardly, the gas in the vibration chamber 4321a is pushed to flow to the fluid channels 4314a, and is discharged out. At the same time, the vibration portion 4332a of the silicon material layer 433a is driven by the actuating portion 4311a to displace downwardly, and the gas in the convergence chamber 422a is compressed to flow to the vibration chamber 4321a. Thereafter, when the piezoelectric component 44a drives the actuating portion 4311a to displace upwardly, the volume of the vibration chamber 4321a is greatly increased, and then there is a higher suction force to inhale the gas into the vibration chamber 4321a. By repeating the above actions, the actuating portion 4311a is continuously driven by the piezoelectric element 44a to displace upwardly and downwardly, and further to drive the vibration portion 4332a to displace upwardly and downwardly. By changing the internal pressure of the MEMS pump 4a, the gas is inhaled and discharged continuously, thereby achieving the actions of the MEMS pump 4a.

Please refer to FIG. 12. When the micro pump 4 is enabled to operate, the gas is inhaled through the air inlet 13 shown in FIG. 1A and is introduced into the accommodation-slot region 12. Moreover, the gas is transported from the air intake hole 411 of the micro pump 4, and continuously guided to the gas-collection chamber 12a. At the same time, the gas flows into the first recessed chamber 11a through the first through holes 11b, and flows into the second recessed chamber 11e through the second through hole 11f. The gas flowing into the first recessed chamber 11a and the second recessed chamber pushes the valve plate 2 upwardly and makes it abut the top cover 3. At this time, the valve plate 2 is pushed against the second protrusion 35a in the discharging chamber 35 by the pushing force generated by the gas flowing into the second recessed chamber 11e from the second through hole 11f. In that, the discharging outlet 32 is closed. Moreover, since the valve plate 2 is spaced apart from the first protrusion 11c of the first recessed chamber 11a, the gas flowing through the second recessed chamber 11e and the first recessed chamber 11a is further transported into the air inlet chamber 34 through the valve hole 21. Whereby, the gas is introduced into the air inlet groove 31 and concentrated in the airbag. The airbag is inflated to achieve the gas collection operation of the blood pressure measurement module. In this way, the blood pressure measurement module is applied to a wearable device (such as a wearable watch). The gas collection operation of the blood pressure measurement module makes the airbag to be tightly attached to the skin of the user wearing it for measurement. With the pressure sensor 6 detecting the pressure change in the airbag, the detection operation is performed to achieve the blood pressure measurement.

Figure 13:
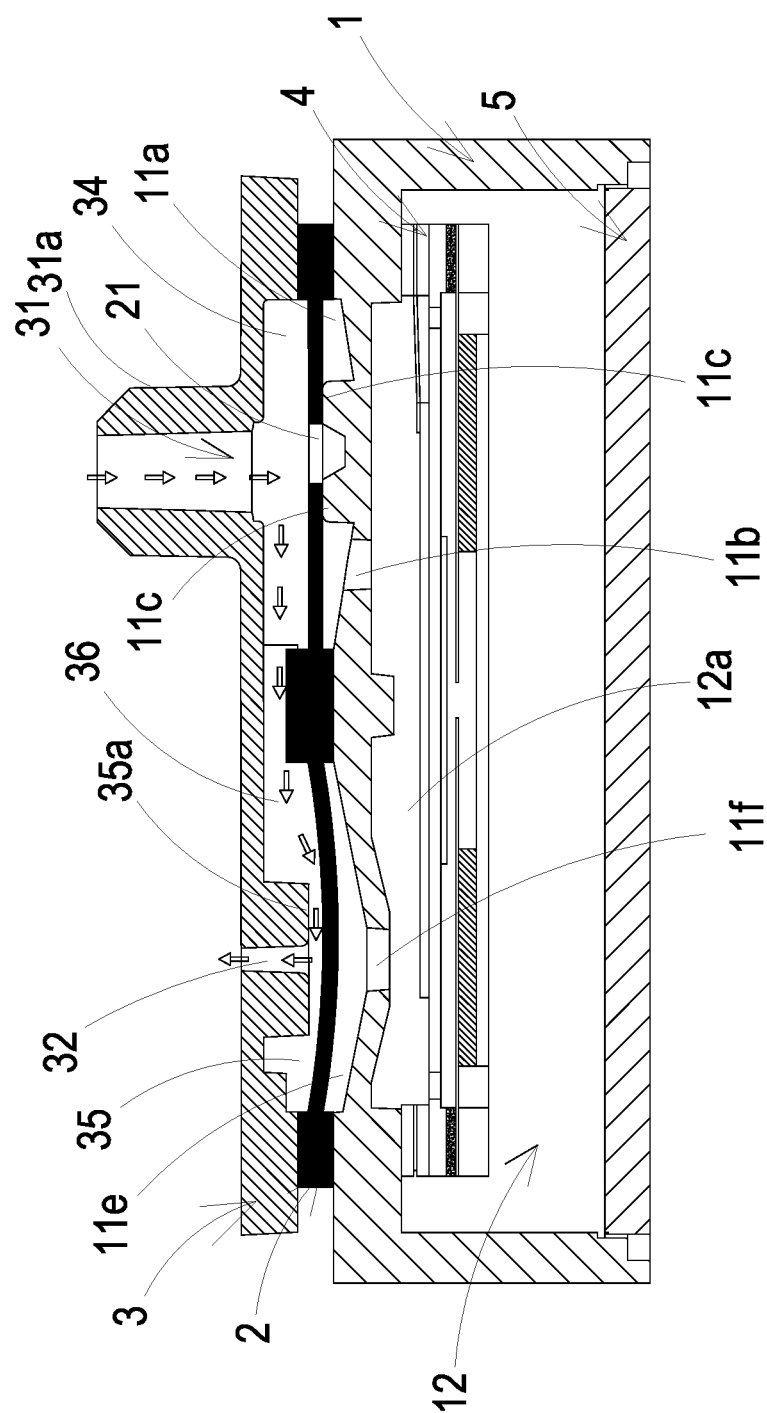
FIG. 13 is a cross-sectional schematic view showing the blood pressure measurement module from the line BB of FIG. 1B performing deflation.

As shown in FIG. 13, after the blood pressure measurement is completed, the operation of the micro pump 4 is stopped. Since the air pressure in the airbag is greater than the air pressure in the air inlet chamber 34, the gas starts to be guided from the inside of the airbag through the air inlet groove 31 to the air inlet chamber 34. At this time, the introduced gas pushes the valve plate 2 to move downwardly, so that the valve hole 21 is closed by the first protrusion 11c. It allows the gas in the air inlet chamber 34 to flow to the discharging chamber 35 through the communication groove 36. In that, the gas introduced into the discharging chamber 35 pushes the valve plate 2 downwardly, and the valve plate 2 is separated away from abutting the second protrusion 35a and pushed to fall into the second recessed chamber 11e. Whereby, the discharging chamber 35 is in fluid communication with the discharging outlet 32, and the gas introduced into the discharging chamber 35 can be discharged through the discharging outlet 32. Thus, the gas in the airbag is released and the rapid deflation operation of the blood pressure measurement module is achieved.

Figure 1B:
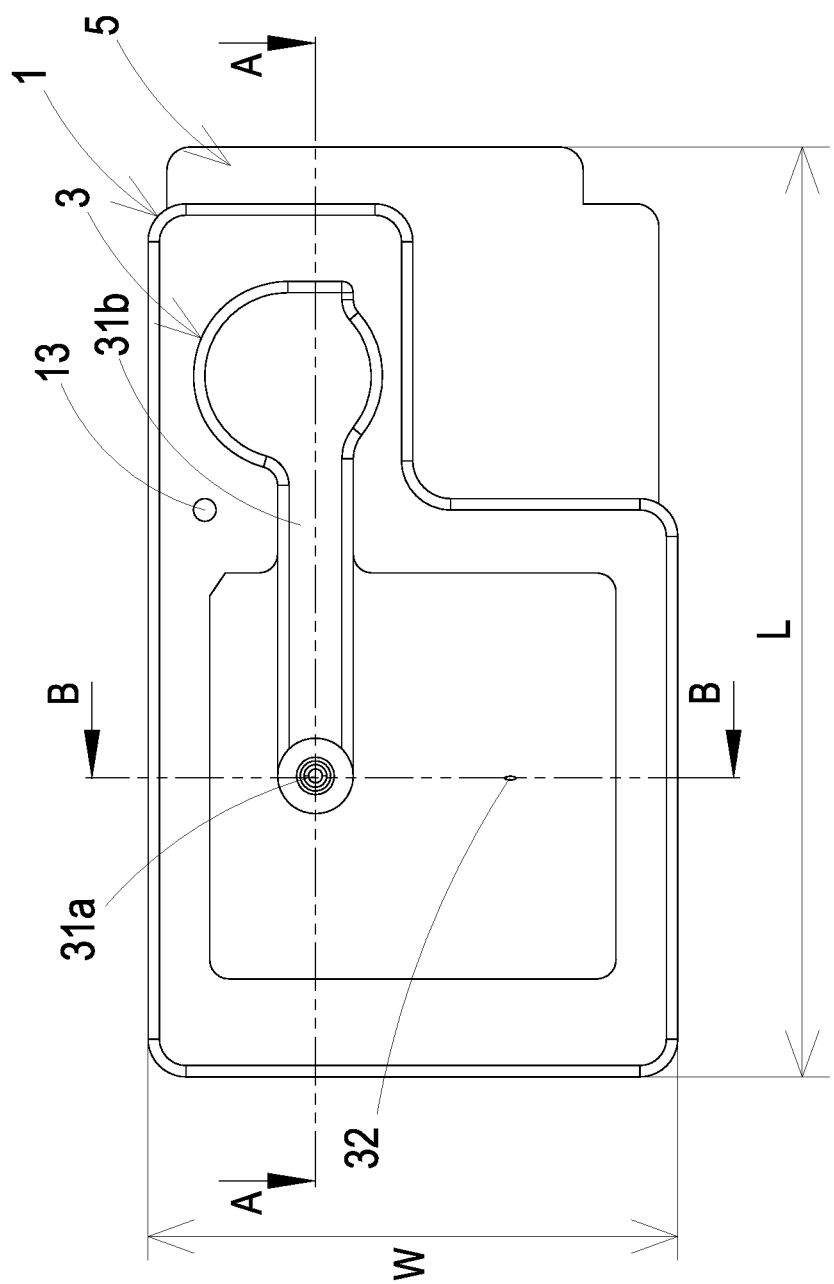
FIG. 1B is a top view illustrating the blood pressure measurement module according to the first embodiment of the present disclosure.
Figure 1C:
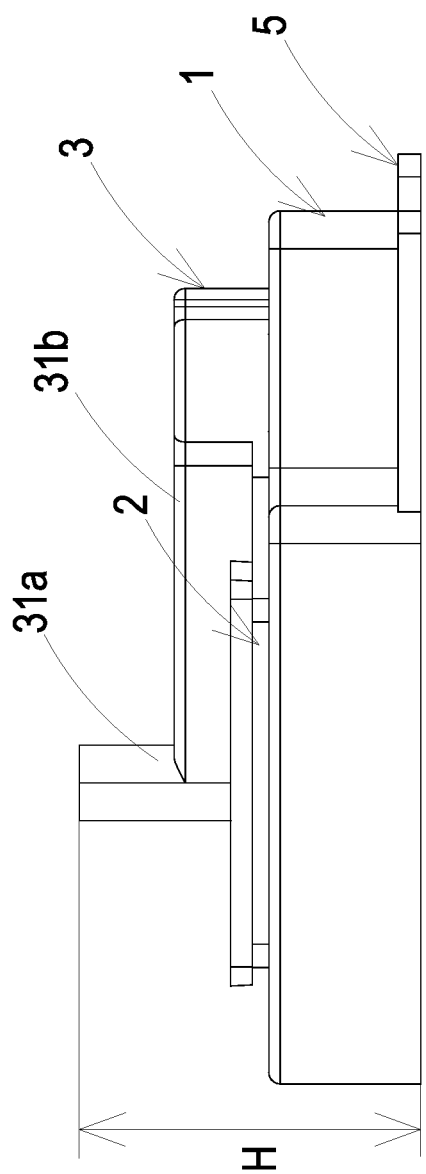
FIG. 1C is a lateral view illustrating the blood pressure measurement module according to the first embodiment of the present disclosure.
Figure 2A:
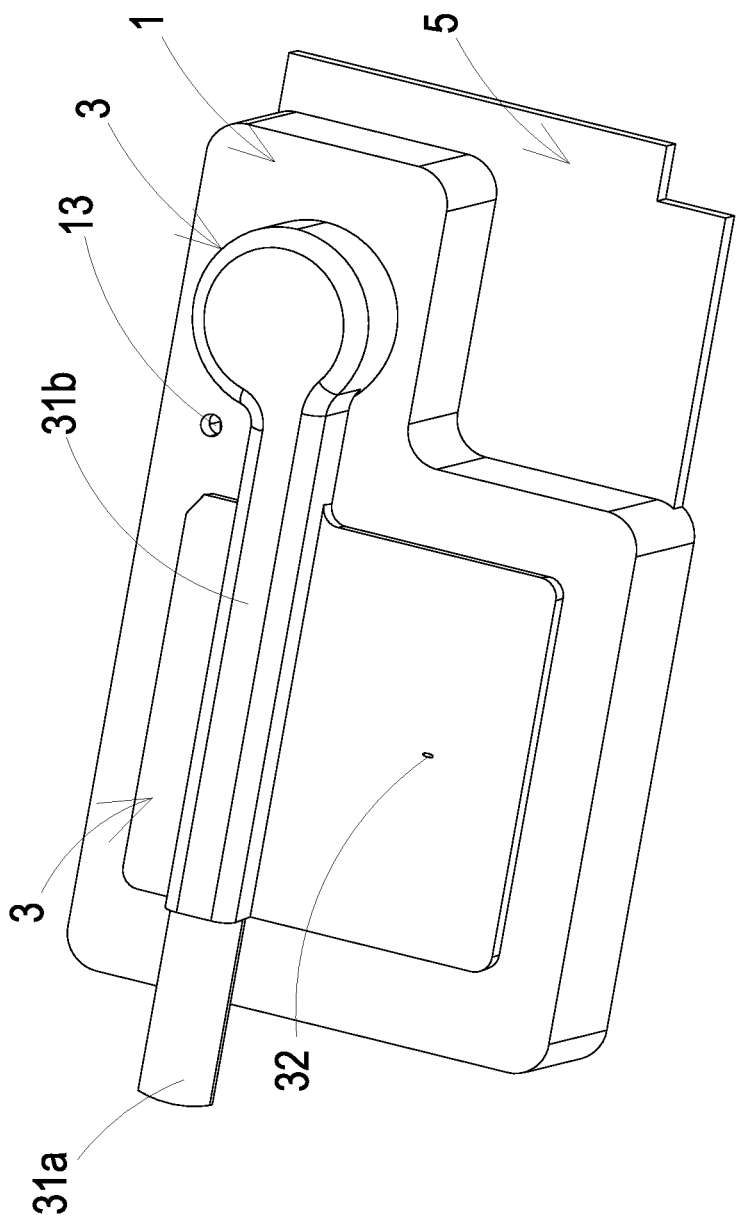
FIG. 2A is a perspective schematic view illustrating a blood pressure measurement module according to a second embodiment of the present disclosure.
Figure 2B:
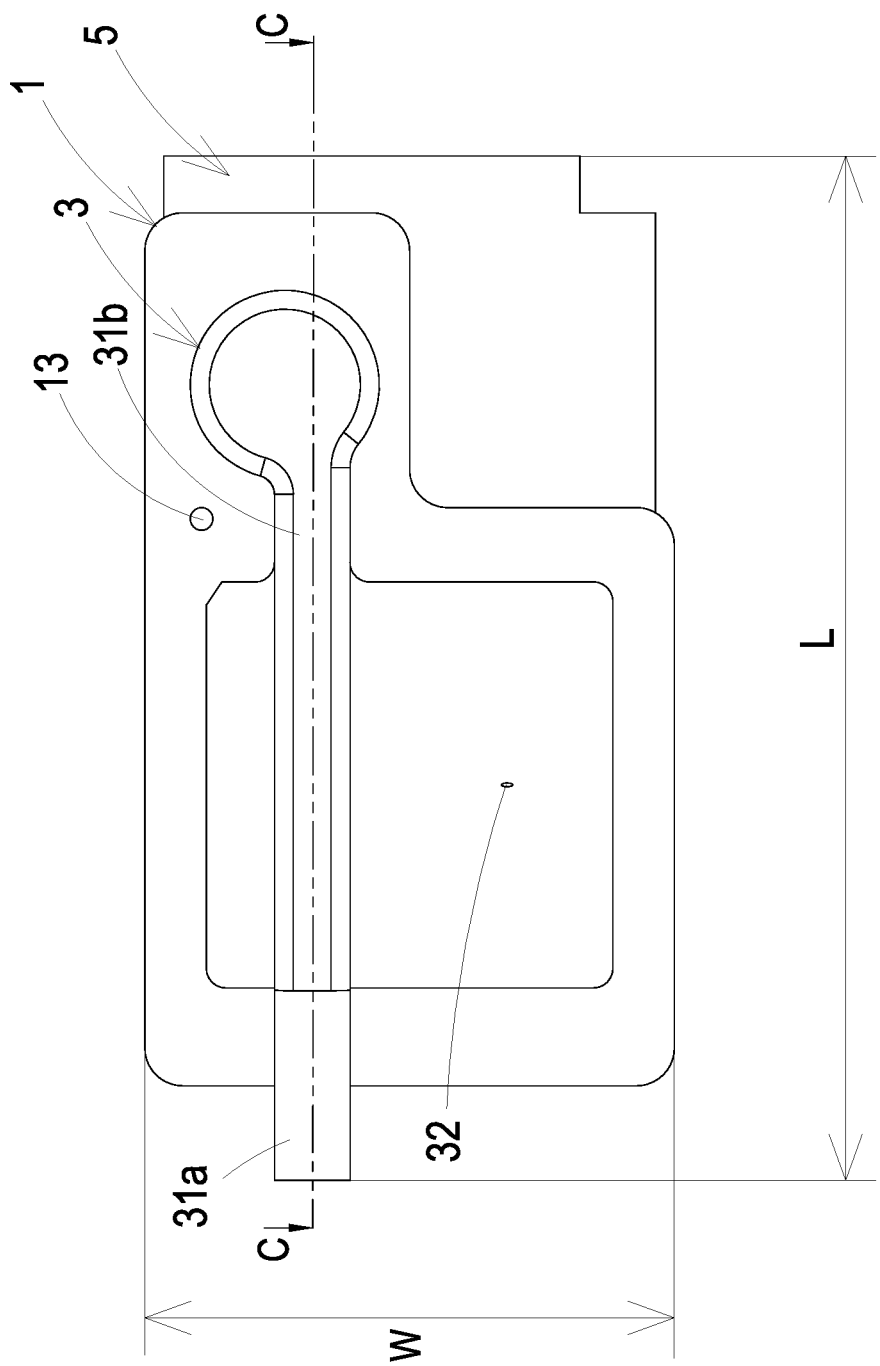
FIG. 2B is a top view illustrating the blood pressure measurement module according to the second embodiment of the present disclosure.
Figure 2C:
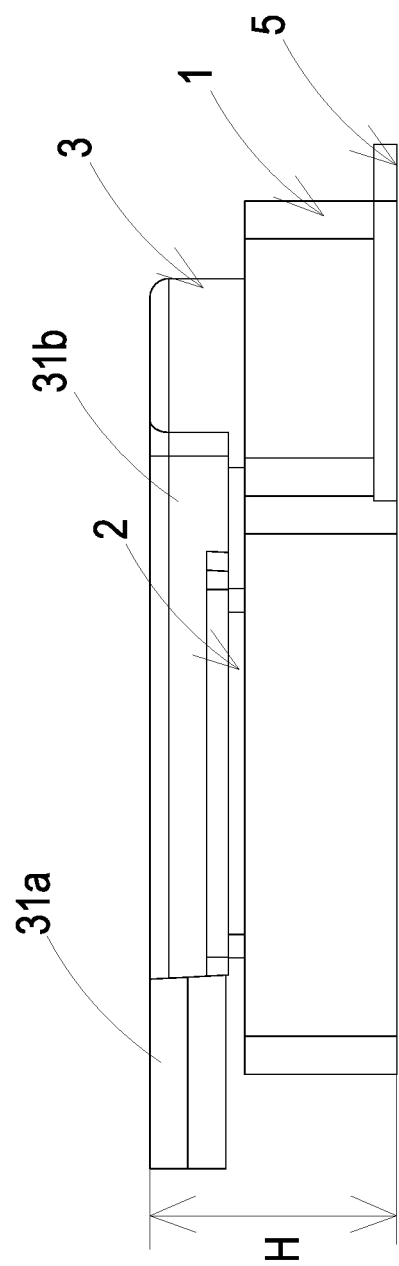
FIG. 2C is a lateral view illustrating the blood pressure measurement module according to the second embodiment of the present disclosure.
Figure 3A:
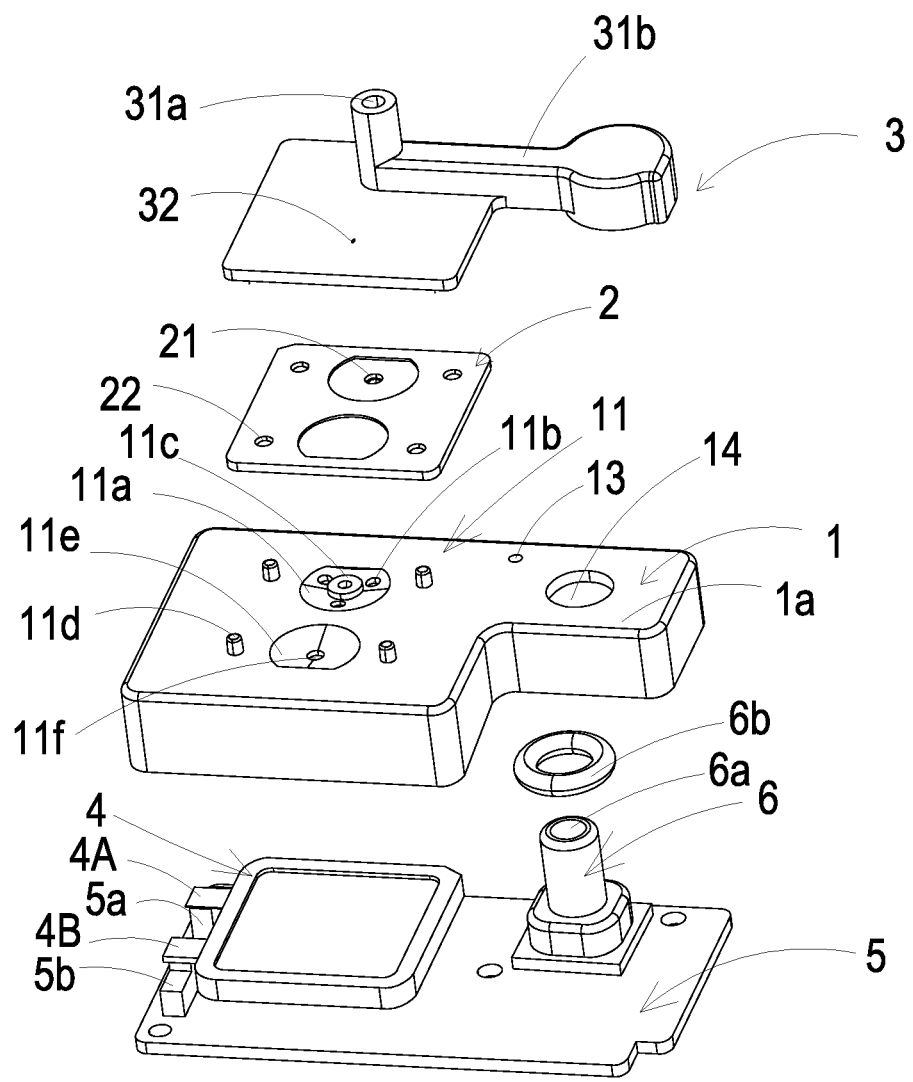
FIG. 3A is an exploded perspective view illustrating the blood pressure measurement module of FIG. 1.
Figure 3B:
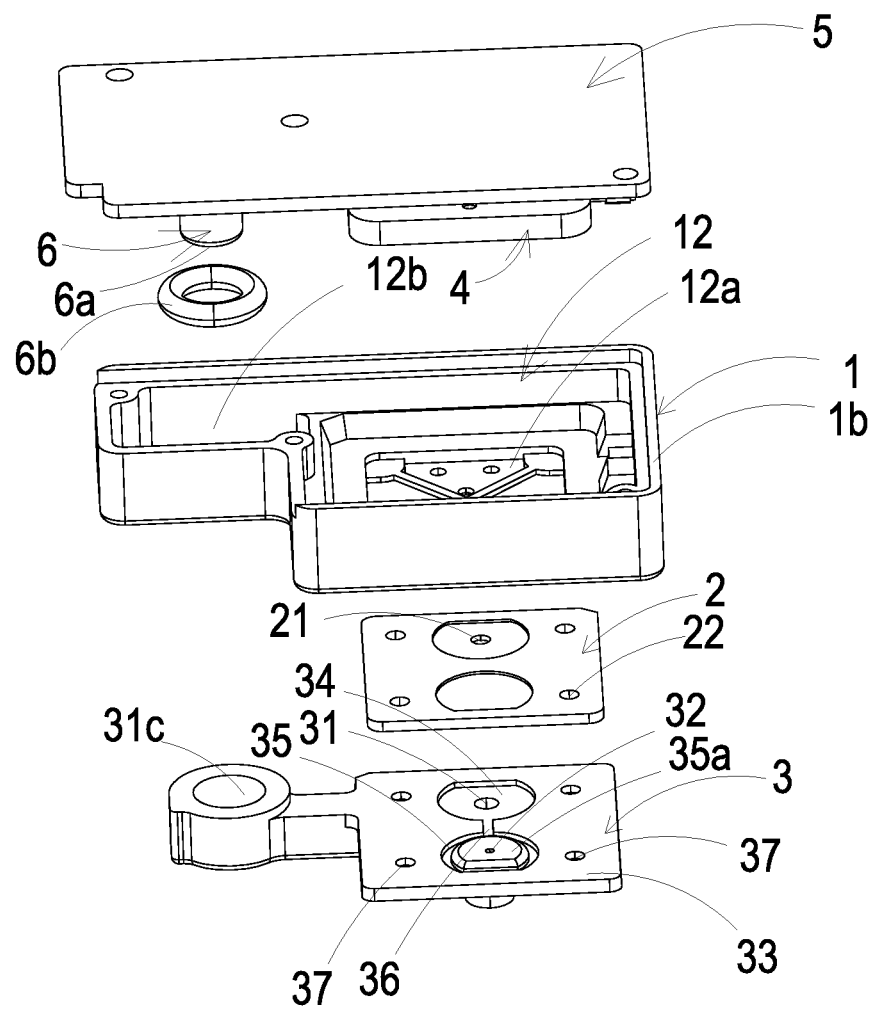
FIG. 3B is an exploded perspective view illustrating the blood pressure measurement module of FIG. 1 from another view angle.

From the above descriptions, the blood pressure measurement module of the present disclosure is assembled on a wearable device (such as a wearable watch) for application, and the overall structure size in the design is considered. Therefore, the blood pressure measurement module of the present disclosure includes the base 1, the valve plate 2, the top cover 3, the micro pump 4, the drive circuit board 5 and the pressure sensor 6 assembled. More particularly, a thin piezoelectric micro pump 4 combined with the pressure sensor 6 is assembled with a miniaturized overall structure design of to a miniaturized base 1, the valve plate 2 and the top cover 3. The blood pressure measurement module is further assembled with an airbag and applied to a wearable device (such as a wearable watch). Rapid inflation and deflation operations are achieved for the blood pressure measurement. The measurement can complete rapid gas collection and pressure relief operations. Please refer to FIG. 1A to 3B. The overall structure of the blood pressure measurement module in the present disclosure is exemplified as the following. In the embodiment, the blood pressure measurement module has a length L ranging from 20 mm to 30 mm, a width W ranging from 10 to 16 mm, and a thickness H ranging from 5 mm to 10 mm. As shown in FIGS. 1A to 1C, preferably but not exclusively, the connection end 31a of the air inlet groove 31 is externally connected to the airbag in a vertical direction. Moreover, the blood pressure measurement module has a length L of 25 mm, a width W of 14 mm, and a thickness H of 9 mm. As shown in FIGS. 2A to 2C, preferably but not exclusively, the connection end 31a of the air inlet groove 31 is externally connected to the airbag in a horizontal direction. The blood pressure measurement module has a length L of 27 mm, a width W of 14 mm, and a thickness H of 6.5 mm. Thus, the optimized size of the blood pressure measurement module is applicable for a wearable device, such as a wearable watch.

Figure 14:
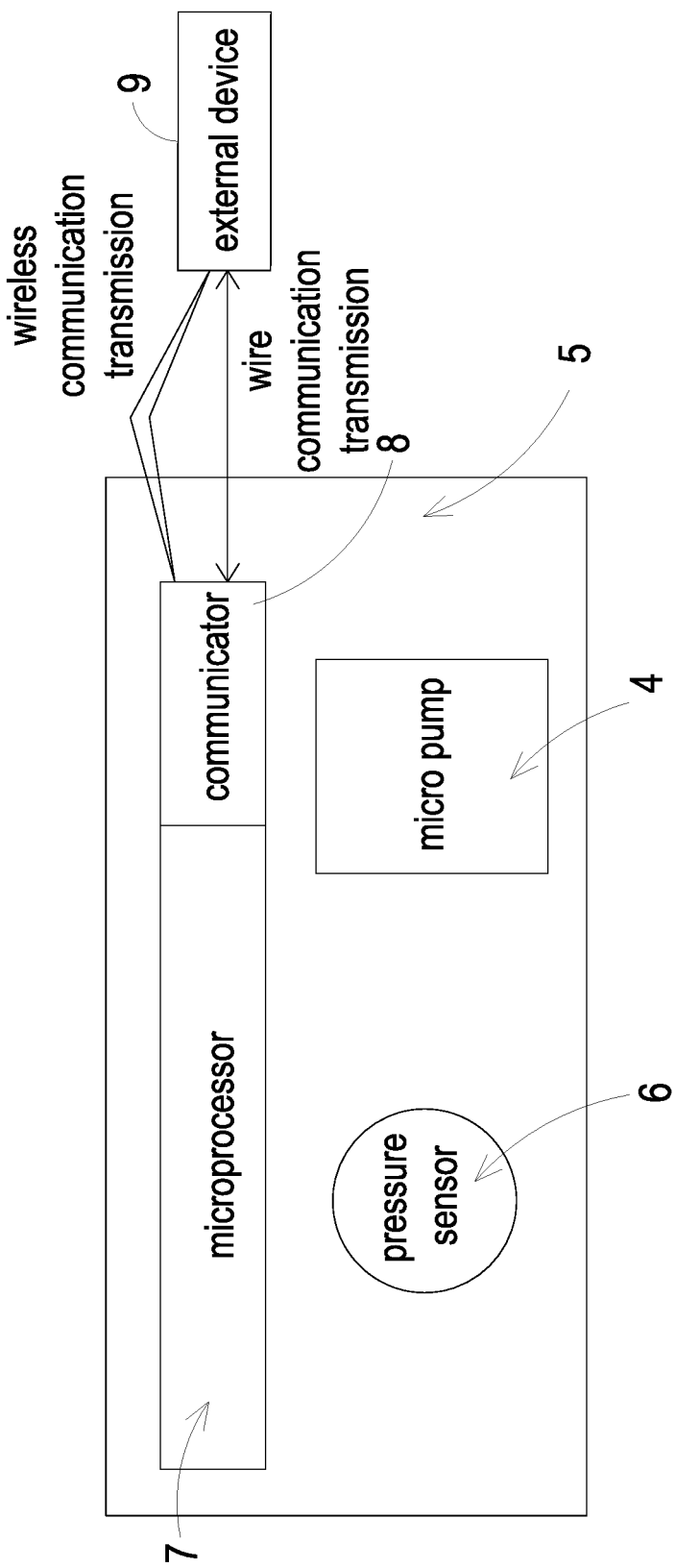
FIG. 14 is a block diagram shows the blood pressure measurement module communicated with an external device according to the embodiment of the present disclosure.

As shown in FIG. 14, the blood pressure measurement module may further include a microprocessor 7 and a communicator 8, which are disposed on the driving circuit board 5. The microprocessor 7 receives measuring signals measured by the pressure sensor 6, and converts the measuring signals into information data. The communicator 8 transmits the information data through a communication transmission to an external device 9 for storage, processing and application. Preferably but not exclusively, the communication transmission is a wired communication transmission or a wireless communication transmission. Preferably but not exclusively, the external device 9 is at least one selected from the group consisting of a cloud system, a portable device and a computer system.

In summary, the present disclosure provides a blood pressure measurement module, which is easily implemented in a blood pressure measurement device. By utilizing an inflatable blood pressure measuring method directly and combining an optical blood pressure measuring method measured by an optical sensor for calibration, the most accurate information of blood pressure measurement value is obtained. In addition, the information is further transmitted through an external connection device to a self-learning artificial intelligence (AI) program, which is responsible for 24-hour analysis and monitoring. It has functions of abnormal feedback and notification warnings, and is highly industrially utilized.

In summary, the blood pressure measurement module is capable of achieving the effects of rapid inflation and deflation of the airbag by disposing the base, the valve plate and the top cover. Furthermore, the size of the pump is greatly reduced by disposing the micro pump. Thus, the blood pressure measurement module is applicable for a wearable device such as a smart watch. It is highly industrially utilized.

While the disclosure has been described in terms of what is presently considered to be the most practical and preferred embodiments, it is to be understood that the disclosure needs not be limited to the disclosed embodiments. On the contrary, it is intended to cover various modifications and similar arrangements included within the spirit and scope of the appended claims which are to be accorded with the broadest interpretation so as to encompass all such modifications and similar structures.

What is claimed is:

1. A blood pressure measurement module comprising:
   a base comprising a valve-carrying region, an accommodation-slot region, an air inlet and a penetration hole, wherein the valve-carrying region and the accommodation-slot region are disposed on different surfaces, respectively, and the air inlet and the penetration hole are in fluid communication with the accommodation-slot region, wherein a first recessed chamber and a second recessed chamber are formed on the valve-carrying region, a plurality of first through holes pass through and are disposed in the first recessed chamber and in fluid communication with the accommodation-slot region, and a first protrusion protrudes from a center of the first recessed chamber, wherein at least one second through hole passes through and is disposed in the second recessed chamber and in fluid communication with the accommodation-slot region, wherein a gas-collection chamber and a sensor chamber are concavely formed in the accommodation-slot region, the sensor chamber is disposed adjacent to and in fluid communication with one side of the gas-collection chamber, and in fluid communication with the air inlet and the penetration hole;
   a valve plate disposed and carried on the valve-carrying region and comprising a valve hole, wherein the valve hole is corresponding in position to the first protrusion;
   a top cover sealed on the valve-carrying region to cover and seal the valve plate and the penetration hole, wherein the top cover comprises an air inlet groove, a discharging outlet and a mounting surface, wherein the air inlet groove and the discharging outlet are spaced apart from each other, the mounting surface correspondingly covers the valve plate, an air inlet chamber is recessed on the mounting surface and in fluid communication with the air inlet groove, and a discharging chamber is recessed on the mounting surface and corresponding in position to the discharging outlet, wherein a second protrusion protrudes from a center of the discharging chamber, and the discharging outlet passes through a center of the second protrusion and is in fluid communication with the discharging chamber, so that the valve plate and the second protrusion abut each other to form a pre-force for closing the discharging outlet, wherein a communication groove is recessed between the air inlet chamber and the discharging chamber, and the air inlet groove is opposed to the mounting surface and in fluid communication with the mounting surface, wherein the air inlet groove comprises a connection end and an extension end, the connection end is externally connected to an airbag, and the extension end is opposed to the connection end, extended to and corresponding in position to the penetration hole, and comprises a cover slot;
   a micro pump disposed in the accommodation-slot region and covering the gas-collection chamber;
   a driving circuit board covering the accommodation-slot region and providing a driving signal for the micro pump, so as to control operations of the micro pump; and;
   a pressure sensor disposed on and electrically connected to the driving circuit board, wherein the pressure sensor is spatially corresponding to the sensor chamber of the accommodation-slot region of the base, correspondingly passes through the penetration hole, and is sleeved in the cover slot of the top cover, so as to communicate with the air inlet groove and communicate with the airbag;
   wherein the micro pump is driven by the driving circuit board to achieve a gas transport, gas outside the base is introduced into the accommodation-slot region through the air inlet, and continuously transported and introduced into the gas-collection chamber to concentrate, so as to allow the gas to push the valve plate away from abutting the first protrusion and flow through the valve hole, whereby the gas flowing through the valve hole is continuously transported and introduced into the air inlet groove of the top cover and concentrated in the airbag, the airbag is inflated to oppress skin of a user under measuring, and the user's blood pressure is measured and calculated through the pressure sensor.

2. The blood pressure measurement module according to claim 1, wherein the valve-carrying region of the base further comprises a plurality of protruding posts, and the valve plate comprises a plurality of positioning holes corresponding to the plurality of protruding posts, respectively, so as to correspondingly receiving the plurality of protruding posts of the valve-carrying region, whereby the valve plate is carried and positioned on the valve-carrying region without offset, and it ensures that the valve hole is corresponding in position to the first protrusion.

3. The blood pressure measurement module according to claim 2, wherein the mounting surface of the top cover further comprises a plurality mounting-surface positioning holes corresponding to the plurality of protruding posts, respectively, so as to correspondingly receiving the plurality of protruding posts of the valve-carrying region, whereby, the valve plate is clamped and positioned between the base and the top cover without offset.

4. The blood pressure measurement module according to claim 1, wherein the connection end of the air inlet groove of the top cover is externally connected to the airbag in a vertical direction.

5. The blood pressure measurement module according to claim 1, wherein the connection end of the air inlet groove of the top cover is externally connected to the airbag in a horizontal direction.

6. The blood pressure measurement module according to claim 1, wherein when the operations of the micro pump is stopped, the gas pressure of the gas collected in the airbag is greater than the gas pressure of the gas-collection chamber, and the gas collected in the airbag is led out through the air inlet groove and pushes the valve plate to keep abutting the first protrusion, so as to close the valve hole, wherein the gas is introduced into the discharging chamber through the communication groove, and introduced to push the valve plate away from abutting the second protrusion, so as to open the discharging outlet, whereby the gas collected in the airbag is discharged outside the top cover through the discharging outlet to achieve a rapid pressure relief operation of the airbag.

7. The blood pressure measurement module according to claim 1, wherein the driving circuit board further comprises a microprocessor and a communicator packaged thereon, wherein the microprocessor receives measuring signals measured by the pressure sensor, and converts the measuring signals into information data, and the communicator transmits the information data through a communication transmission to an external device for storage, processing and application.

8. The blood pressure measurement module according to claim 7, wherein the communication transmission is a wired communication transmission or a wireless communication transmission.

9. The blood pressure measurement module according to claim 7, wherein the external device is at least one selected from the group consisting of a cloud system, a portable device and a computer system.

10. The blood pressure measurement module according to claim 1, wherein the micro pump comprises:
  an inlet plate having at least one air intake hole, at least one convergence channel and a convergence chamber, wherein the at least one air intake hole is disposed to inhale the gas, and the at least one convergence channel is disposed corresponding in position to the air intake hole to guide the gas inhaled from the air intake hole to the convergence chamber;
  a resonance plate disposed on the inlet plate and having a central aperture and a movable part, wherein the central aperture is corresponding in position to the convergence chamber of the inlet plate, and the movable part surrounds the central aperture; and
  a piezoelectric actuator corresponding in position to the resonance plate;
  wherein the inlet plate, the resonance plate and the piezoelectric actuator are sequentially stacked, and a chamber space is formed between the resonance plate and the piezoelectric actuator, so that when the piezoelectric actuator is driven, the gas introduced from the at least one air intake hole of the inlet plate is converged to the convergence chamber through the at least one convergence channel, and flows through the central aperture of the resonance plate so as to produce a resonance by the movable part of the resonance plate and the piezoelectric actuator to transport the gas.

11. The blood pressure measurement module according to claim 10, wherein the piezoelectric actuator comprises:
  a suspension plate being square-shaped and being permitted to undergo a bending vibration;
  an outer frame surrounding the suspension plate;
  at least one bracket connected between the suspension plate and the outer frame for providing an elastic support; and
  a piezoelectric element having a side, wherein a length of the side of the piezoelectric element is less than or equal to that of the suspension plate, and the piezoelectric element is attached on a surface of the suspension plate, wherein when a voltage is applied to the piezoelectric element, the suspension plate is driven to undergo the bending vibration.

12. The blood pressure measurement module according to claim 10, wherein the piezoelectric actuator comprises:
  a suspension plate being square-shaped and being permitted to undergo a bending vibration;
  an outer frame surrounding the suspension plate;
  at least one bracket connected between the suspension plate and the outer frame for providing an elastic support, wherein a surface of the suspension plate and a surface of the outer frame are non-coplanar, and the chamber space is maintained between the surface of the suspension plate and the resonance plate; and
  a piezoelectric element having a side, wherein a length of the side of the piezoelectric element is less than or equal to that of the suspension plate, and the piezoelectric element is attached on a surface of the suspension plate, wherein when a voltage is applied to the piezoelectric element, the suspension plate is driven to undergo the bending vibration.

13. The blood pressure measurement module according to claim 10, wherein the micro pump further comprises:
  a first insulation plate;
  a conductive plate; and
  a second insulation plate;
  wherein, the inlet plate, the resonance plate, the piezoelectric actuator, the first insulation plate, the conductive plate and the second insulation plate are stacked sequentially.

14. The blood pressure measurement module according to claim 1, wherein the micro pump is a micro-electromechanical-systems (MEMS) micro pump comprising:
  a first substrate having a plurality of inlet apertures, wherein the plurality of inlet aperture are tapered-shaped;
  a first oxidation layer stacked on the first substrate, wherein the first oxidation layer comprises a plurality of convergence channels and a convergence chamber, and the plurality of convergence channels are in fluid communication between the convergence chamber and the plurality of inlet apertures;
  a second substrate combined with the first substrate and comprising:
    a silicon chip layer, comprising:
      an actuating portion being in a circular shape;
      an outer peripheral portion being in a hollow ring shape and disposed around the actuating portion;
      a plurality of connecting portions connected between the actuating portion and the outer peripheral portion, respectively; and
      a plurality of fluid channels disposed around the actuating portion and located between the connecting portions;
    a second oxidation layer formed on the silicon chip layer and being in a hollow ring shape, wherein a vibration chamber is collaboratively defined by the second oxidation layer and the silicon chip layer; and
    a silicon material layer being in a circular shape, disposed on the second oxidation layer and bonded to the first oxidation layer, comprising:
      a through hole formed at a center of the silicon material layer;
      a vibration portion disposed around the through hole; and
      a fixing portion disposed around the vibration portion; and a piezoelectric component being in a circular shape and stacked on the actuating portion of the silicon chip layer.

15. The blood pressure measurement module according to claim 14, wherein the piezoelectric component comprises:
a lower electrode layer;
a piezoelectric layer stacked on the lower electrode layer; and
an insulation layer disposed a partial surface of the piezoelectric layer and a partial surface of the lower electrode layer; and
an upper electrode layer stacked on the insulation layer and a remaining surface of the piezoelectric layer without the insulation layer disposed thereon, so as to electrically connect with piezoelectric layer.

16. The blood pressure measurement module according to claim 1, wherein the blood pressure measurement module has a length ranging from 20 mm to 30 mm, a width ranging from 10 to 16 mm, and a thickness ranging from 5 mm to 10 mm.

17. The blood pressure measurement module according to claim 1, wherein the blood pressure measurement module has a length of 25 mm, a width of 14 mm, and a thickness of 9 mm.

18. The blood pressure measurement module according to claim 1, wherein the blood pressure measurement module has a length of 27 mm, a width of 14 mm, and a thickness of 6.5 mm.

* * * * *